(12) United States Patent
Stalcup

(10) Patent No.: US 11,589,908 B2
(45) Date of Patent: Feb. 28, 2023

(54) ORTHOPAEDIC TRAUMA DEVICES WITH POROUS REGIONS AND THERAPEUTIC AGENT DELIVERY

(71) Applicant: SMed-TA/TD, LLC, Columbia City, IN (US)

(72) Inventor: Gregory C. Stalcup, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 440 days.

(21) Appl. No.: 16/905,412

(22) Filed: Jun. 18, 2020

(65) Prior Publication Data

US 2020/0397494 A1 Dec. 24, 2020

Related U.S. Application Data

(60) Provisional application No. 62/864,001, filed on Jun. 20, 2019.

(51) Int. Cl.
| | |
|---|---|
| *A61B 17/86* | (2006.01) |
| *A61B 17/74* | (2006.01) |
| *A61B 17/92* | (2006.01) |
| *A61B 17/34* | (2006.01) |
| *A61B 17/88* | (2006.01) |
| *A61L 27/54* | (2006.01) |

(52) U.S. Cl.
CPC ........ *A61B 17/864* (2013.01); *A61B 17/3423* (2013.01); *A61B 17/744* (2013.01); *A61B 17/746* (2013.01); *A61B 17/8822* (2013.01); *A61B 17/921* (2013.01); *A61L 27/54* (2013.01); *A61L 2430/02* (2013.01)

(58) Field of Classification Search
CPC .... A61B 17/921; A61B 17/744; A61B 17/864
See application file for complete search history.

(56) References Cited

U.S. PATENT DOCUMENTS

| | | | | |
|---|---|---|---|---|
| 4,175,555 | A * | 11/1979 | Herbert ................ | A61B 17/863 606/304 |
| 8,372,126 | B2 * | 2/2013 | Trieu ................... | A61B 17/864 606/76 |
| 2001/0021852 | A1 * | 9/2001 | Chappius ........... | A61B 17/3472 600/300 |
| 2008/0046091 | A1 | 2/2008 | Weiss et al. | |

(Continued)

FOREIGN PATENT DOCUMENTS

WO 2010/025386 A1 3/2010

OTHER PUBLICATIONS

Extended European Search Report dated Oct. 9, 2020 for European Patent Application No. 20 18 0974 (6 pages).

*Primary Examiner* — Christian A Sevilla
(74) *Attorney, Agent, or Firm* — Taylor IP, P.C.

(57) ABSTRACT

A device for treating orthopaedic trauma includes a device body having an exterior surface and a cannulation formed therein that extends from one longitudinal end of the device body to an opposite longitudinal end of the device body and at least one porous ingrowth material region associated with the exterior surface of the device body and fluidly coupled to the cannulation. The at least one porous ingrowth material region is configured to deliver a therapeutic agent from the cannulation to a region outside the device body.

19 Claims, 27 Drawing Sheets

(56) References Cited

U.S. PATENT DOCUMENTS

| | | | |
|---|---|---|---|
| 2011/0125265 A1* | 5/2011 | Bagga | A61B 17/7098 623/16.11 |
| 2012/0172934 A1* | 7/2012 | Fisher | A61B 17/8858 606/92 |
| 2015/0038941 A1 | 2/2015 | Nebosky et al. | |

* cited by examiner

ORTHOPAEDIC TRAUMA DEVICES WITH POROUS REGIONS AND THERAPEUTIC AGENT DELIVERY

CROSS REFERENCE TO RELATED APPLICATIONS

This is a non-provisional application based upon U.S. provisional patent application Ser. No. 62/864,001, entitled "ORTHOPAEDIC TRAUMA DEVICES WITH POROUS REGIONS AND THERAPEUTIC AGENT DELIVERY", filed Jun. 20, 2019, which is incorporated herein by reference.

BACKGROUND OF THE INVENTION

1. Field of the Invention

The present invention relates to orthopaedic devices, and, more particularly, to orthopaedic devices for trauma treatment.

2. Description of the Related Art

Many different systems for treating orthopaedic trauma are known. Many systems include at least one device that is implanted in a fractured bone to bring one or more bone fragments back into contact with the bone and repair the bone. While such systems are generally effective at treating orthopaedic trauma, many different types of failure modes exist that detrimentally affect healing of the bone.

What is needed in the art is a system for treating orthopaedic trauma that is less susceptible to failure than known systems.

SUMMARY OF THE INVENTION

The present invention provides systems for treating orthopaedic trauma that include at least one device with a cannulated device body and one or more porous ingrowth material regions that are fluidly coupled to a cannulation formed in the device body for delivering a therapeutic agent to a region outside the device body.

In some exemplary embodiments provided according to the present invention, a device for treating orthopaedic trauma includes a device body having an exterior surface and a cannulation formed therein that extends from one longitudinal end of the device body to an opposite longitudinal end of the device body and at least one porous ingrowth material region associated with the exterior surface of the device body and fluidly coupled to the cannulation. The at least one porous ingrowth material region is configured to deliver a therapeutic agent from the cannulation to a region outside the device body.

In some exemplary embodiments provided according to the present invention, an orthopaedic trauma treatment system includes a first device and a second device coupled to the first device. The first device includes a first device body having an exterior surface and a cannulation formed therein that extends from one longitudinal end of the device body to an opposite longitudinal end of the device body and at least one first porous ingrowth material region associated with the exterior surface of the first device body and fluidly coupled to the cannulation. The at least one first porous ingrowth material region is configured to deliver a therapeutic agent from the cannulation to a region outside the first device body. The second device coupled to the first device includes a second device body having at least one second porous ingrowth material region.

One possible advantage that may be realized by exemplary embodiments provided according to the present invention is that the porous ingrowth material region(s) of the device can help stably fixate the device in a bone following implantation to reduce the risk of the device becoming unstable.

Another possible advantage that may be realized by exemplary embodiments provided according to the present invention is that fluidly coupling the porous ingrowth material region(s) to the cannulation allows for therapeutic agent delivery to occur through the porous ingrowth material region(s), which can further encourage tissue ingrowth and repair.

Yet another possible advantage that may be realized by exemplary embodiments provided according to the present invention is that the system can be implanted using known surgical techniques.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
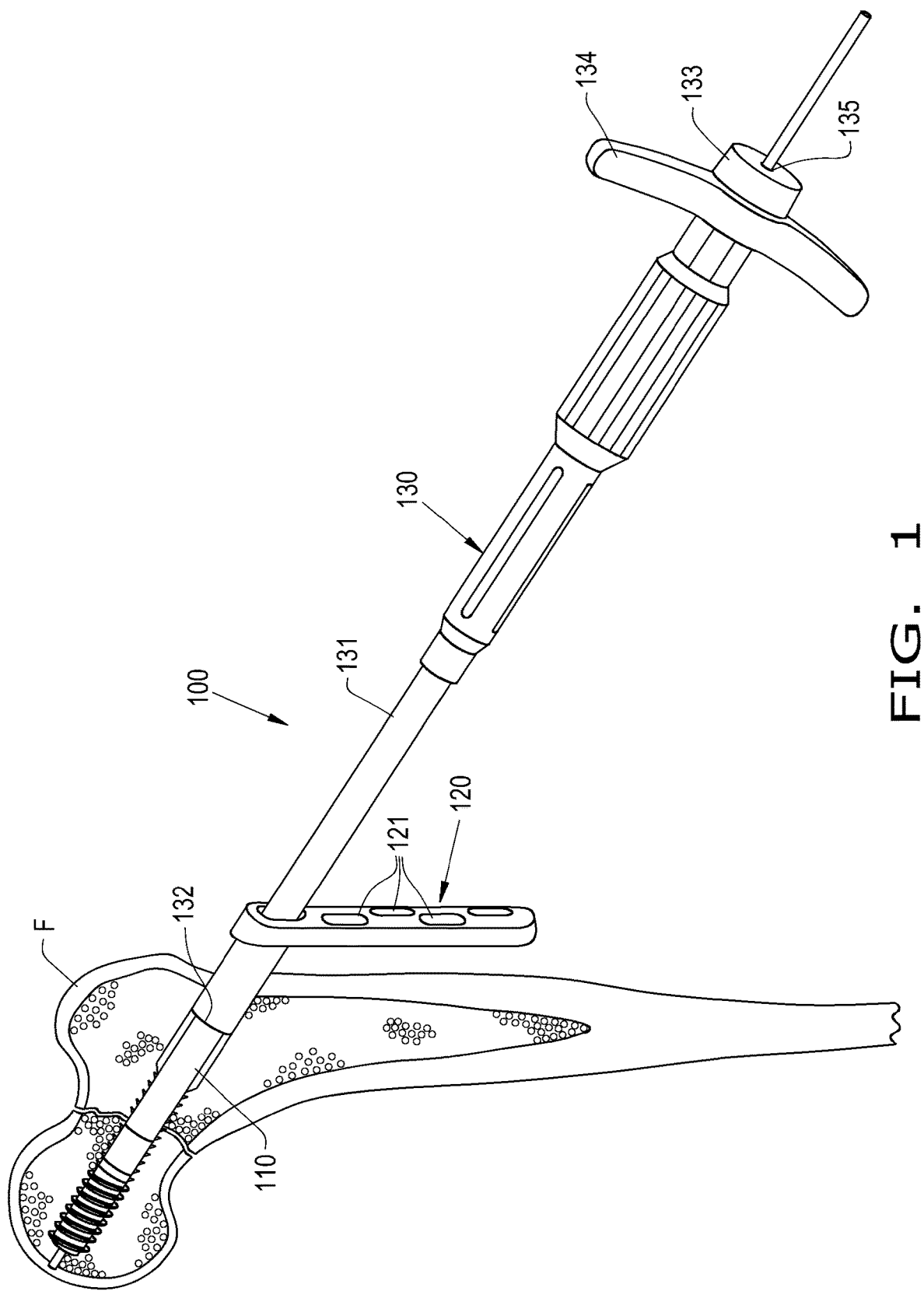
FIG. 1 is a perspective view of an exemplary embodiment of an orthopaedic trauma treatment system provided according to the present invention being implanted in a bone, which is illustrated in a partial cutaway view.
Figure 2:
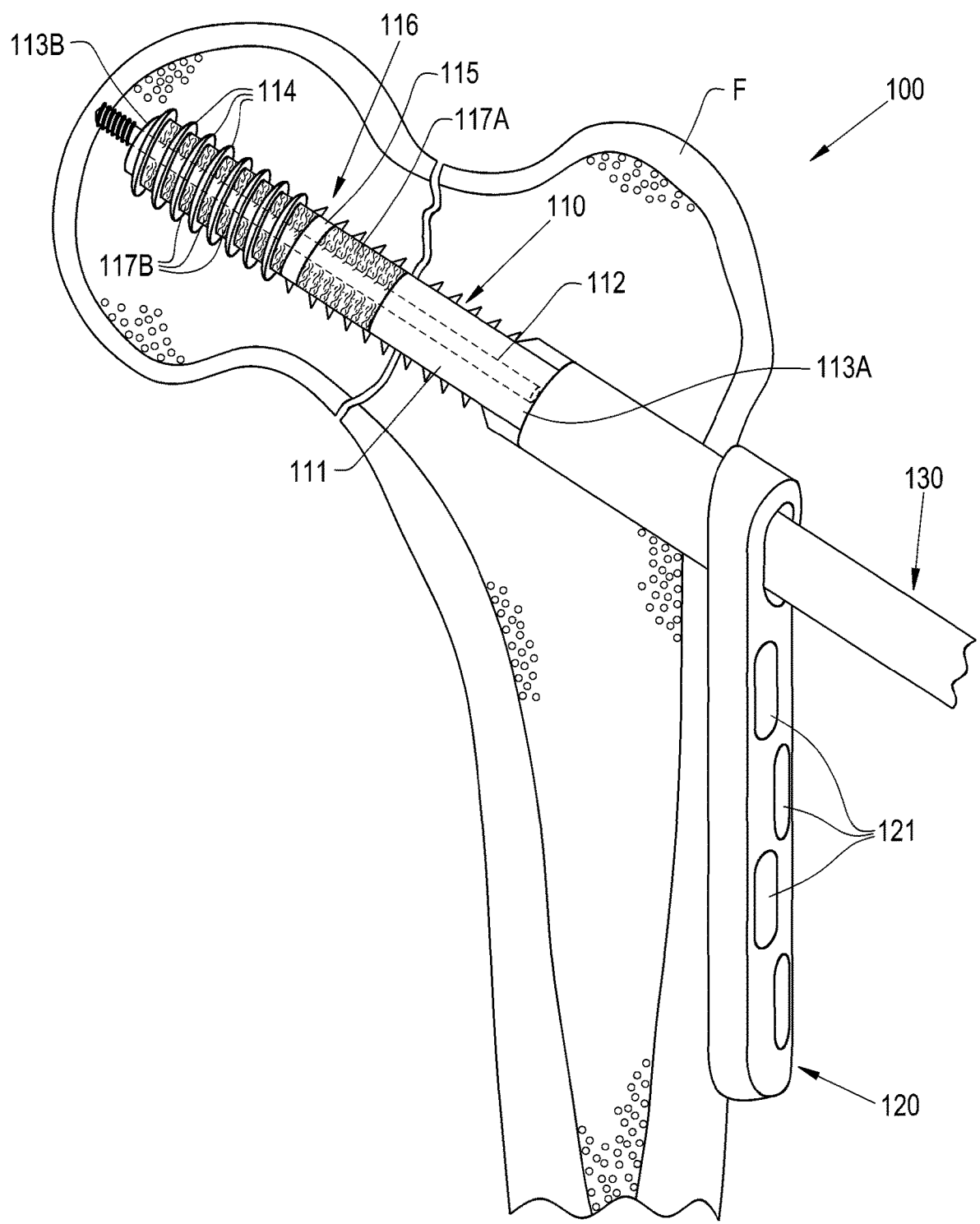
FIG. 2 is another perspective view of the orthopaedic trauma treatment system of FIG. 1 showing greater detail of a lag screw and a bone plate of the system.
Figure 3:
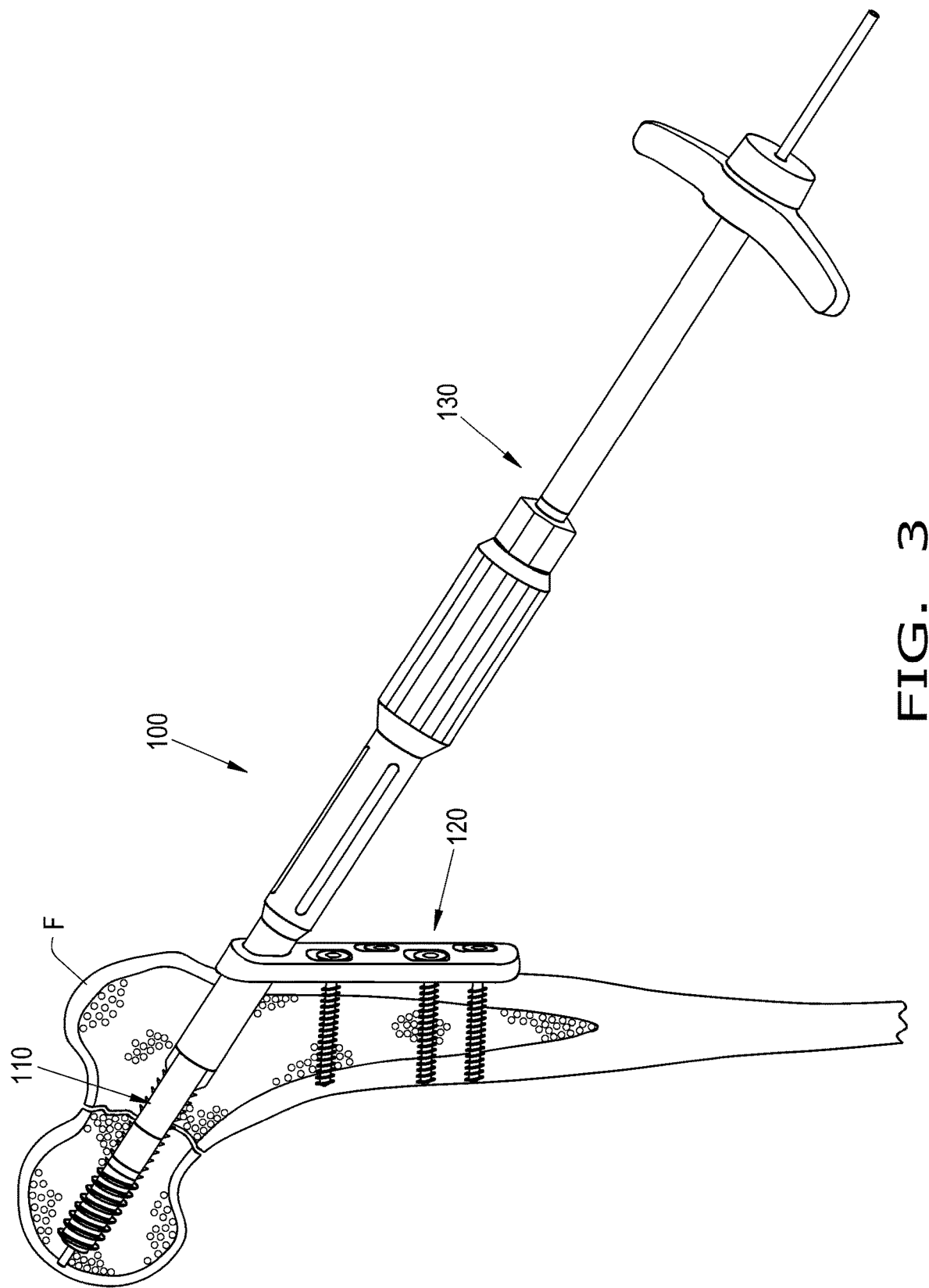
FIG. 3 is another perspective view of the orthopaedic trauma treatment system of FIGS. 1-2 after the bone plate has been fixed to the bone by bone screws.

Referring now to the drawings, and more particularly to FIGS. 1-6, an exemplary embodiment of an orthopaedic trauma treatment system 100 is illustrated that generally includes a first device for treating orthopaedic trauma in the form of a lag screw 110, a bone plate 120 coupled to the lag screw 110, and an installation assembly 130 for installing the lag screw 110 and the bone plate 120 to a bone such as, for example, a femur F. The bone plate 120 may be of a known construction and include several openings 121 that are sized to accept fixation screws to stably fixate the bone plate 120 and the coupled lag screw 110 to the femur F. The number of openings 121 and the distribution of the openings 121 in the bone plate 120 may be varied, as desired. Similarly, the installation assembly 130 may be of a known construction and include a cannulated tubular portion 131 with a first end 132 that is sized and shaped to rotate the lag screw 110 and a second end 133 that has a handle portion 134 that a user, such as a surgeon, may hold and twist to rotate the lag screw 110. Many different types of suitable installation assemblies are known, so further description is omitted for brevity.

Figure 4:
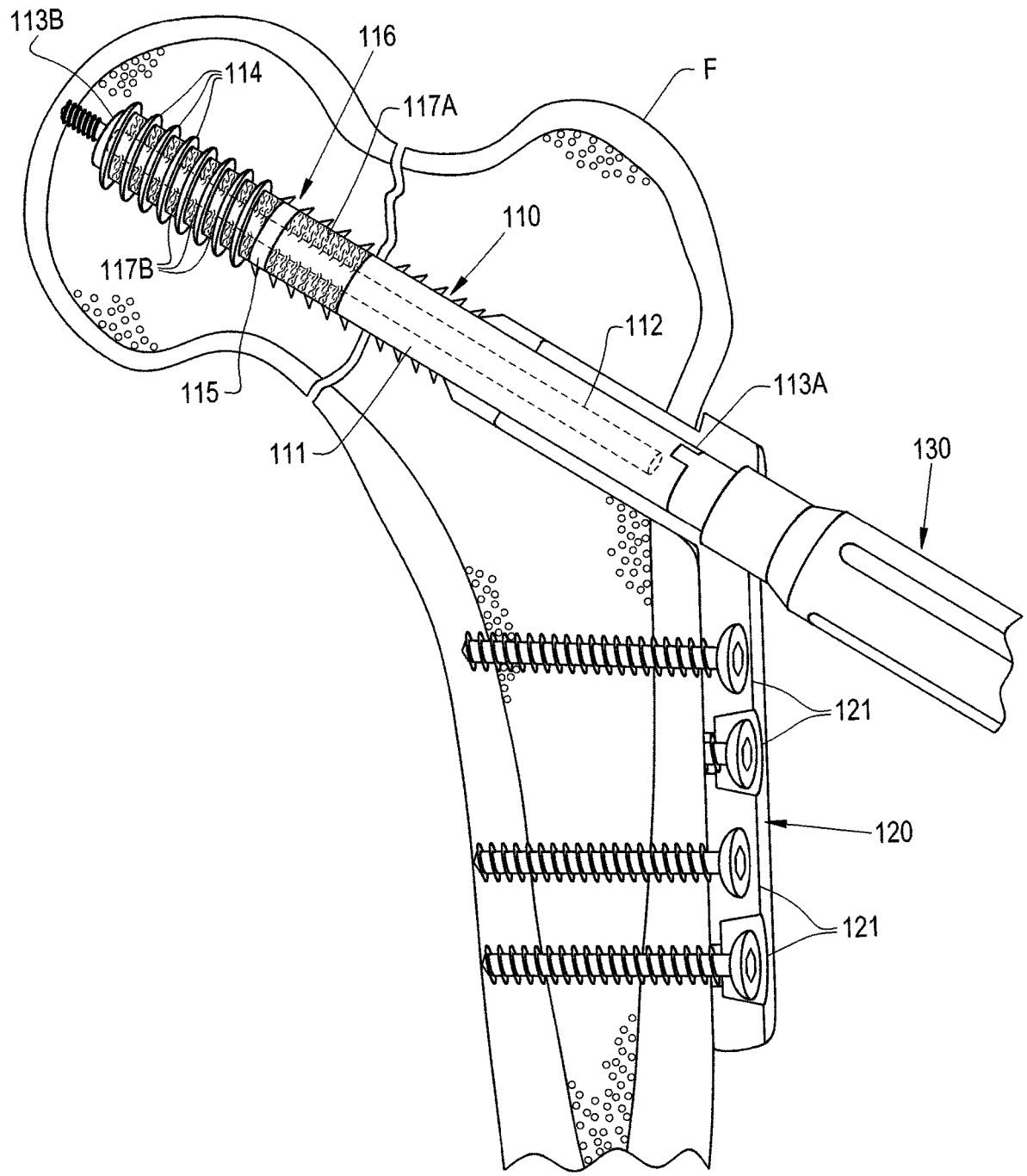
FIG. 4 is another perspective view of the orthopaedic trauma treatment system of FIGS. 1-3 after the bone plate has been fixed to the bone by bone screws.
Figure 5:
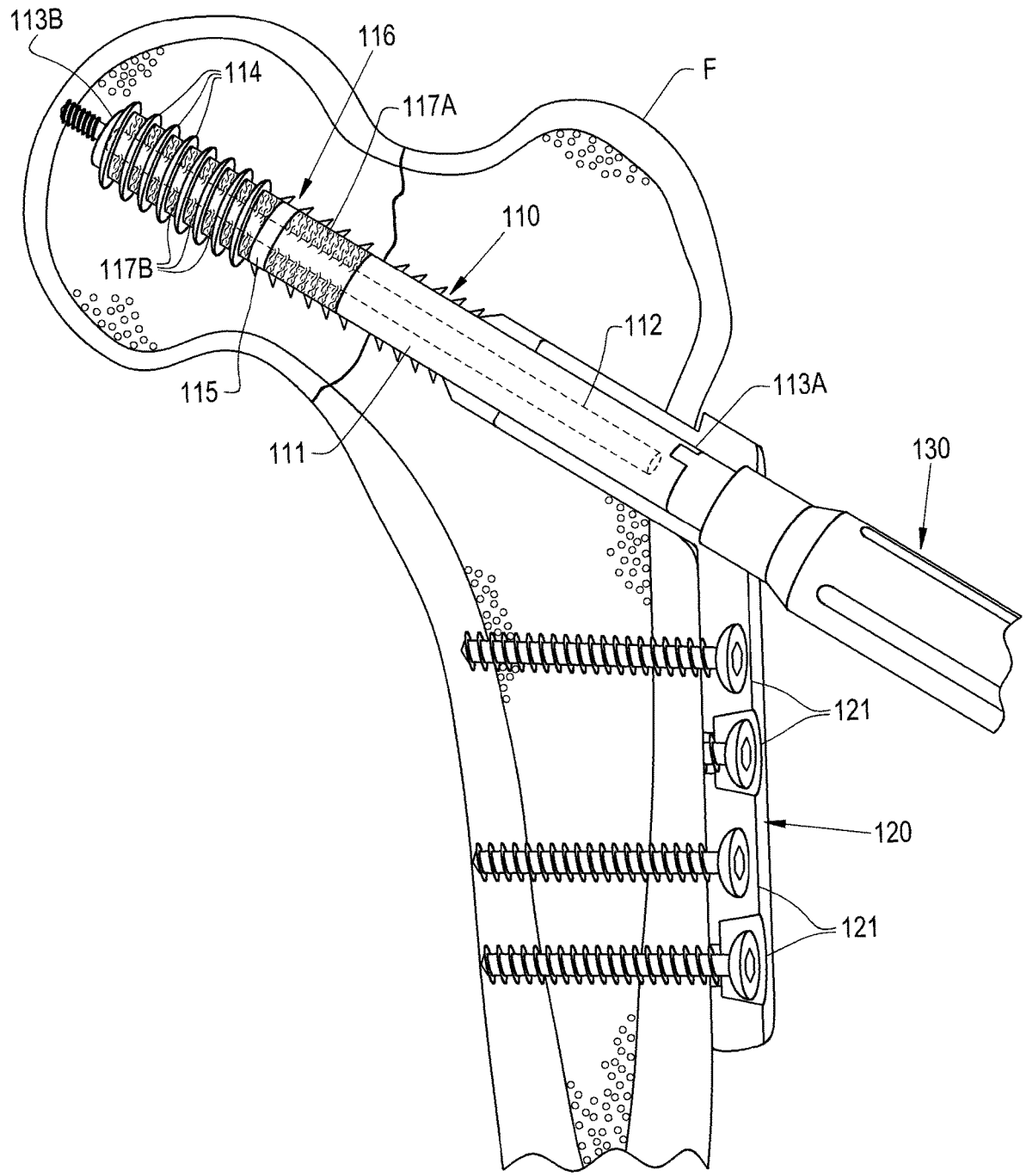
FIG. 5 is a perspective view of the orthopaedic trauma treatment system of FIGS. 1-4 after the lag screw has been displaced to bring a bone fragment back into contact with the rest of the bone.
Figure 6:
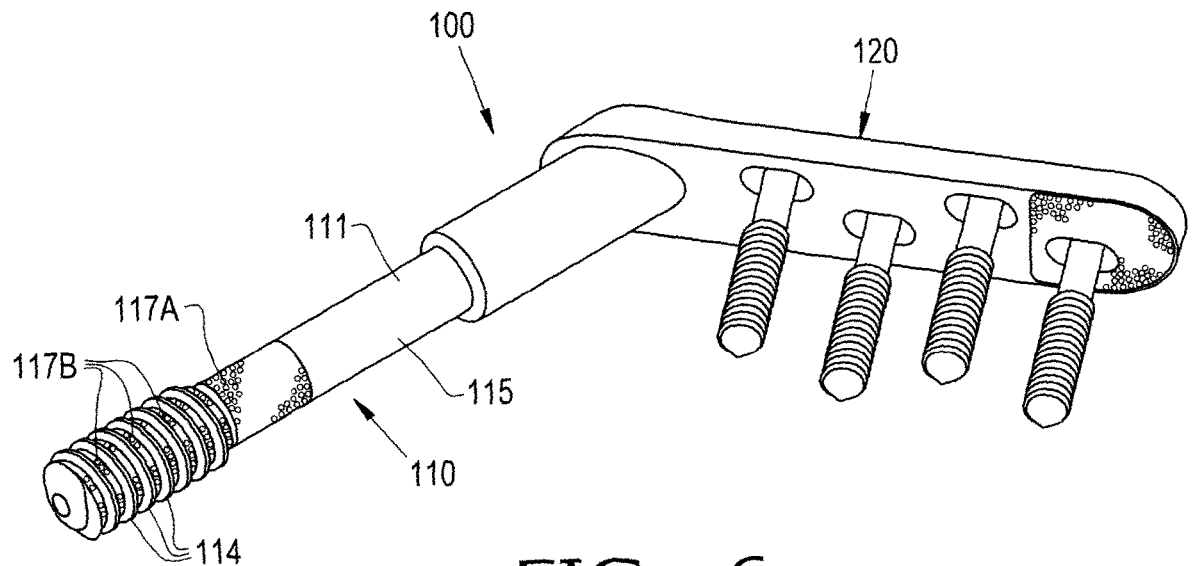
FIG. 6 is a perspective view of the orthopaedic trauma treatment system of FIGS. 1-5 separate from the bone.

The lag screw 110 may be cannulated and include a cylindrical screw body 111, which may also be referred to as a "device body," with a cannulation 112 that extends between two longitudinal ends 113A, 113B of the device body 111 and also include a plurality of threads 114 formed in an exterior surface 115 of the device body 111. Many different sizes and shapes of threads are known and may be utilized in the lag screw 110. As illustrated, the lag screw 110 has a length that is chosen so the lag screw 110 resides in the femoral shaft and a bone fragment, shown as the femoral head and neck. As illustrated in FIGS. 4-5, once the lag screw 110 is seated in the bone fragment of the femur F, the lag screw 110 can be displaced to pull the bone fragment back into contact with the rest of the femur F and promote healing of the femur F. After the bone fragment is back in contact with the rest of the femur, the lag screw 110 and the bone plate 120 act as fixation to hold the fragment in place so the tissue of the fragment can reintegrate with the rest of the femur F and heal.

To encourage stable fixation of the bone fragment, the lag screw 110 includes a fragment fixating portion 116, which may include the threads 114, that has one or more porous ingrowth material regions 117A, 117B disposed on the exterior surface 115 of the device body 111. As illustrated in FIGS. 1-5, one of the porous ingrowth material regions 117A may be placed on the lag screw 110 to reside near a fracture in the bone F when the lag screw 110 is implanted and multiple porous ingrowth material regions 117B may be placed in the space between the threads 114 of the lag screw 110. In some embodiments, the material of the lag screw 110 other than the porous ingrowth material regions 117A, 117B is substantially non-porous or minimally porous, such as a non-porous titanium, so minimal tissue ingrowth occurs into the lag screw 110 other than in the porous ingrowth material regions 117A, 117B. As used herein, "substantially non-porous" corresponds to a porosity of less than 5%, "minimally porous" corresponds to a porosity of less than 20%, and "porous" corresponds to a porosity of at least 20%, such as at least 60%. The material of the porous ingrowth material regions 117A, 117B may be, for example, a porous titanium or polyether ether ketone (PEEK) material that encourages cell and tissue ingrowth. An exemplary material that may be used to form the porous ingrowth material regions 117A, 117B is commercially sold under the tradename OSTEO-SYNC® by SITES MEDICAL® of Columbia City, Ind. It should be appreciated that the number, placement, and amount of material in the porous ingrowth material regions 117A, 117B may be adjusted to achieve different fixation characteristics.

In known lag screws that are used to treat orthopaedic trauma, especially femoral trauma, one of the main failure modes that occur are near the femoral head. The implanted lag screws do not tend to achieve sufficient fixation in the cancellous bone tissue to remain stable and thus have a significant risk of wobbling or falling out after implantation. Thus, insufficient fixation of the lag screw may not only extend the time that it takes for the bone fragment to heal but, in some cases, can actually cause additional damage.

The lag screw 110 provided in accordance with the present disclosure addresses some of these issues by incorporating the porous ingrowth material regions 117A, 117B. The porous ingrowth material regions 117A, 117B provide areas into which surrounding bone tissue can integrate to stably fixate the lag screw 110. When using certain materials, such as the previously described OSTEOSYNC®, a high degree of fixation can occur rapidly to stably fixate the lag screw 110 in the bone F. Therefore, the lag screw 110 provided in accordance with the present disclosure is less prone to wobbling and falling out due to insufficient fixation.

Figure 7:
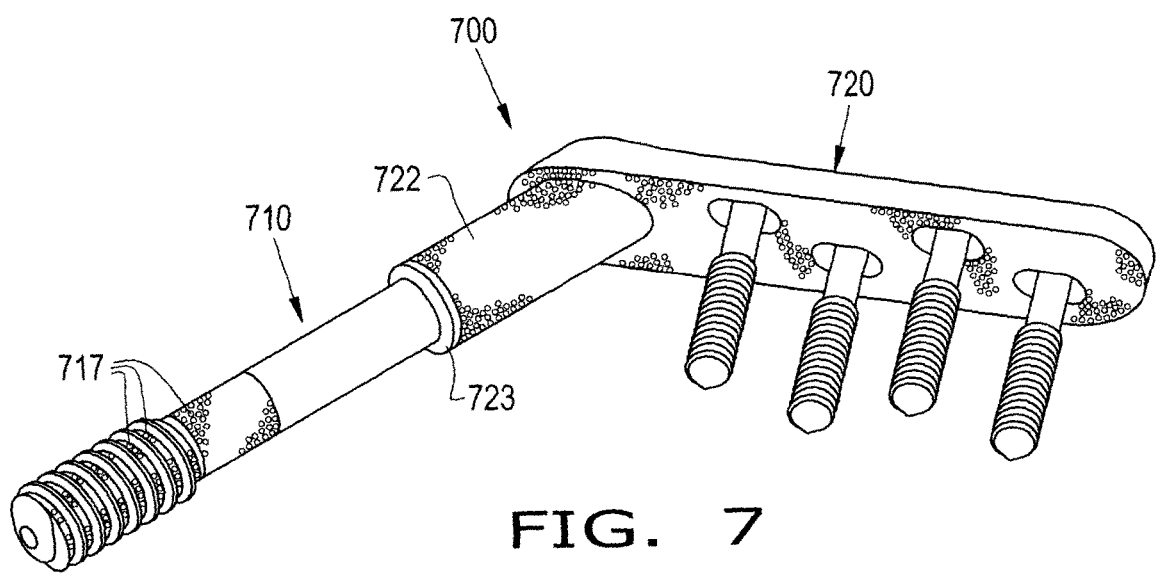
FIG. 7 is a perspective view of another exemplary embodiment of an orthopaedic trauma treatment system provided according to the present invention that includes a bone plate with a neck that has a porous ingrowth material region disposed thereon.
Figure 8:
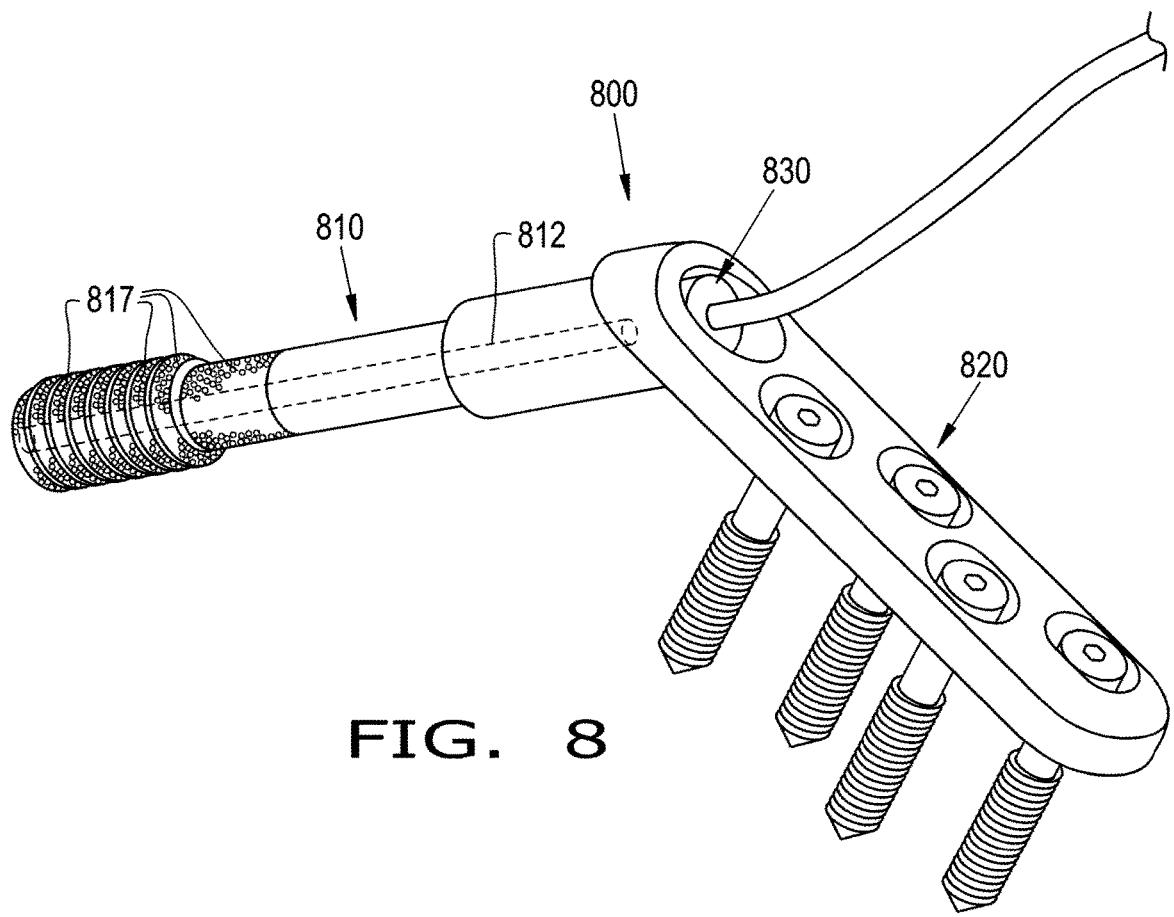
FIG. 8 is a perspective view of another exemplary embodiment of an orthopaedic trauma treatment system provided according to the present invention that has a therapeutic interface coupled to a cannulation of a lag screw.
Figure 9:
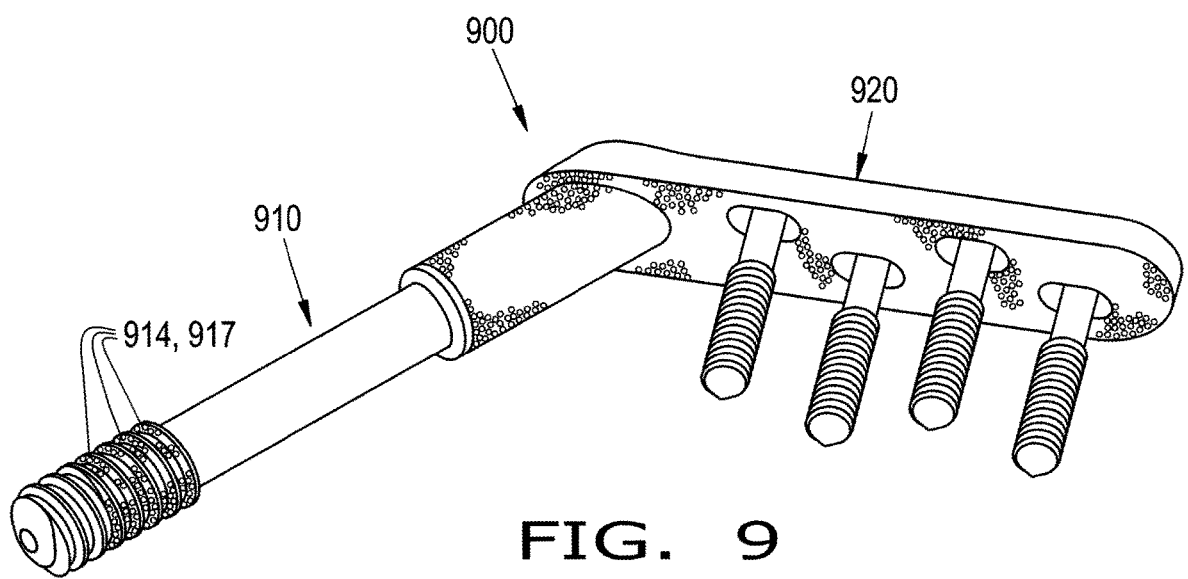
FIG. 9 is a perspective view of another exemplary embodiment of an orthopaedic trauma treatment system provided according to the present invention that has a lag screw including a plurality of threads that are formed as porous ingrowth material regions.

Referring now to FIGS. 7-9, additional exemplary embodiments of orthopaedic trauma treatment systems 700, 800, 900 are illustrated that include bone plates 720, 820, 920 and lag screws 710, 810, 910 with porous ingrowth material regions 717, 817, 917. The trauma treatment system 700 illustrated in FIG. 7 is similar to the system 100 of FIGS. 1-6, with an additional porous ingrowth material region 722 being added to a neck 723 of the bone plate 720 for additional fixation. The trauma treatment system 800 illustrated in FIG. 8 is similar to the system 100 of FIGS. 1-6, but has a therapeutic interface 830 coupled to a cannulation 812 of the lag screw 810 for delivering therapeutic agents, as will be described further herein. The trauma treatment system 900 illustrated in FIG. 9 is similar to the trauma treatment system 700 illustrated in FIG. 7, but some threads 914 of the lag screw 910 are formed as porous ingrowth material regions 917 rather than porous ingrowth material regions being placed between the threads 914. It should thus be appreciated that many variations of orthopaedic trauma treatment systems 100, 700, 800, 900 may be formed according to the present disclosure.

Referring now to FIGS. 10-14, the orthopaedic trauma treatment system 100 of FIGS. 1-6 is illustrated being used to deliver therapeutic agents to the implantation site within the femur F. As used herein, a "therapeutic agent" may be any substance or combination of substances that may be administered to the implantation site to achieve therapeutic effect. Exemplary therapeutic agents include, but are not limited to, anti-microbial agents, anti-inflammatories, anesthetics, growth factors such as bone morphogenetic proteins (BMPs), and stem cells.

Figure 10:
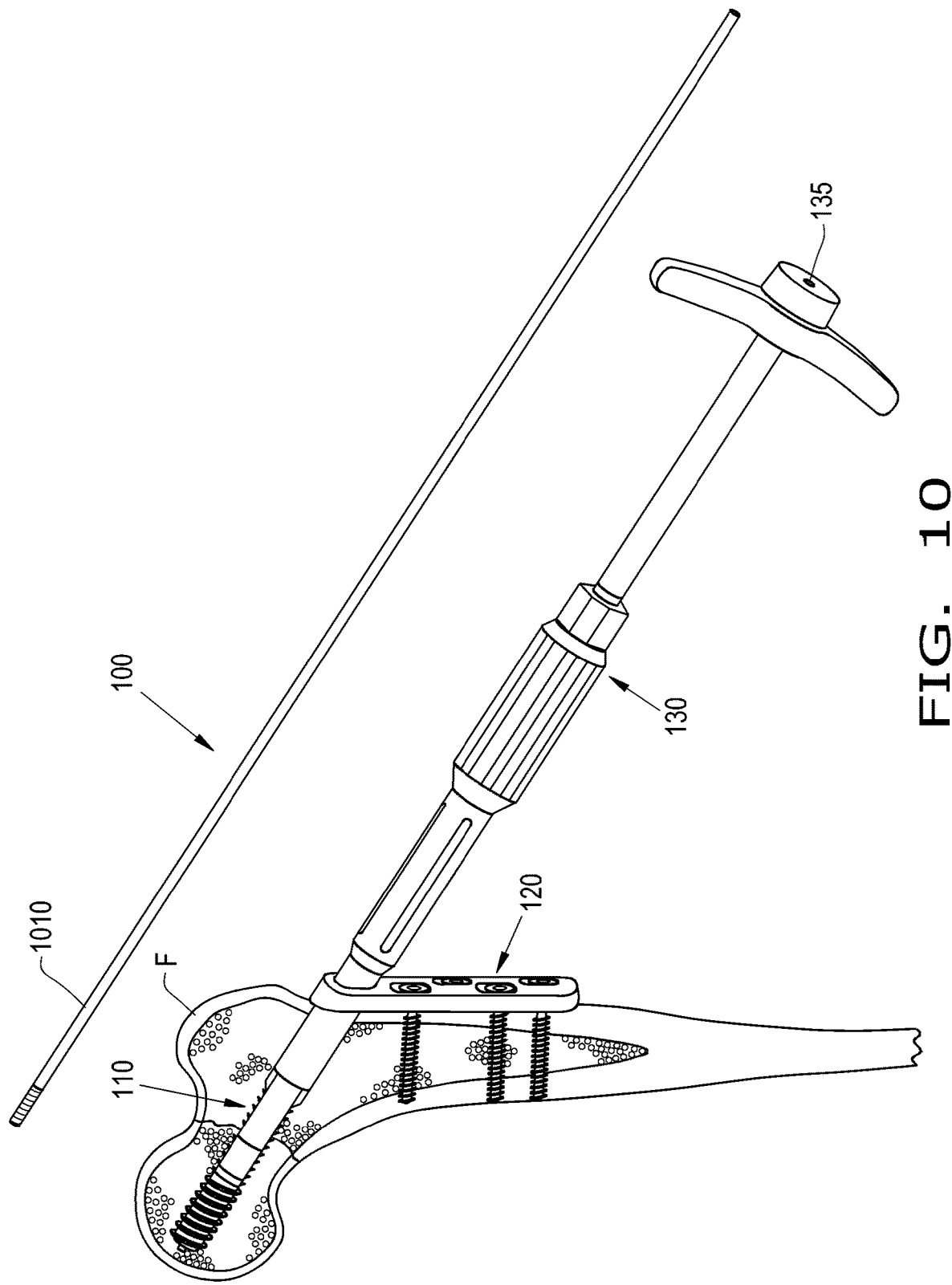
FIG. 10 is a perspective view of the orthopaedic trauma treatment system of FIGS. 1-6 after a guide rod that is used to guide placement of the lag screw is removed from the bone.
Figure 11:
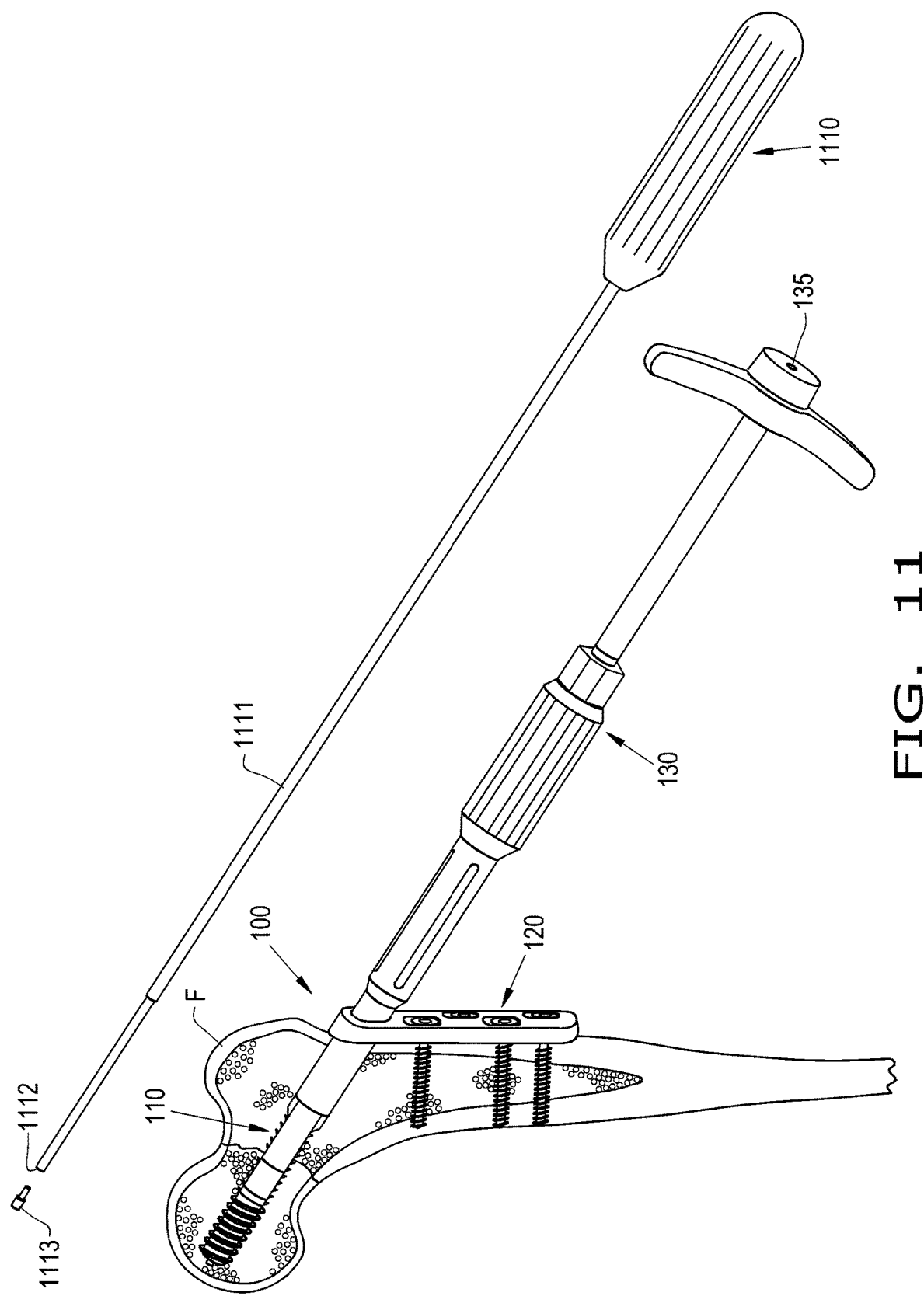
FIG. 11 is a perspective view of the orthopaedic trauma treatment system of FIGS. 1-6 and 10 and an injector that is configured to be placed in a cannulation of the lag screw.
Figure 12:
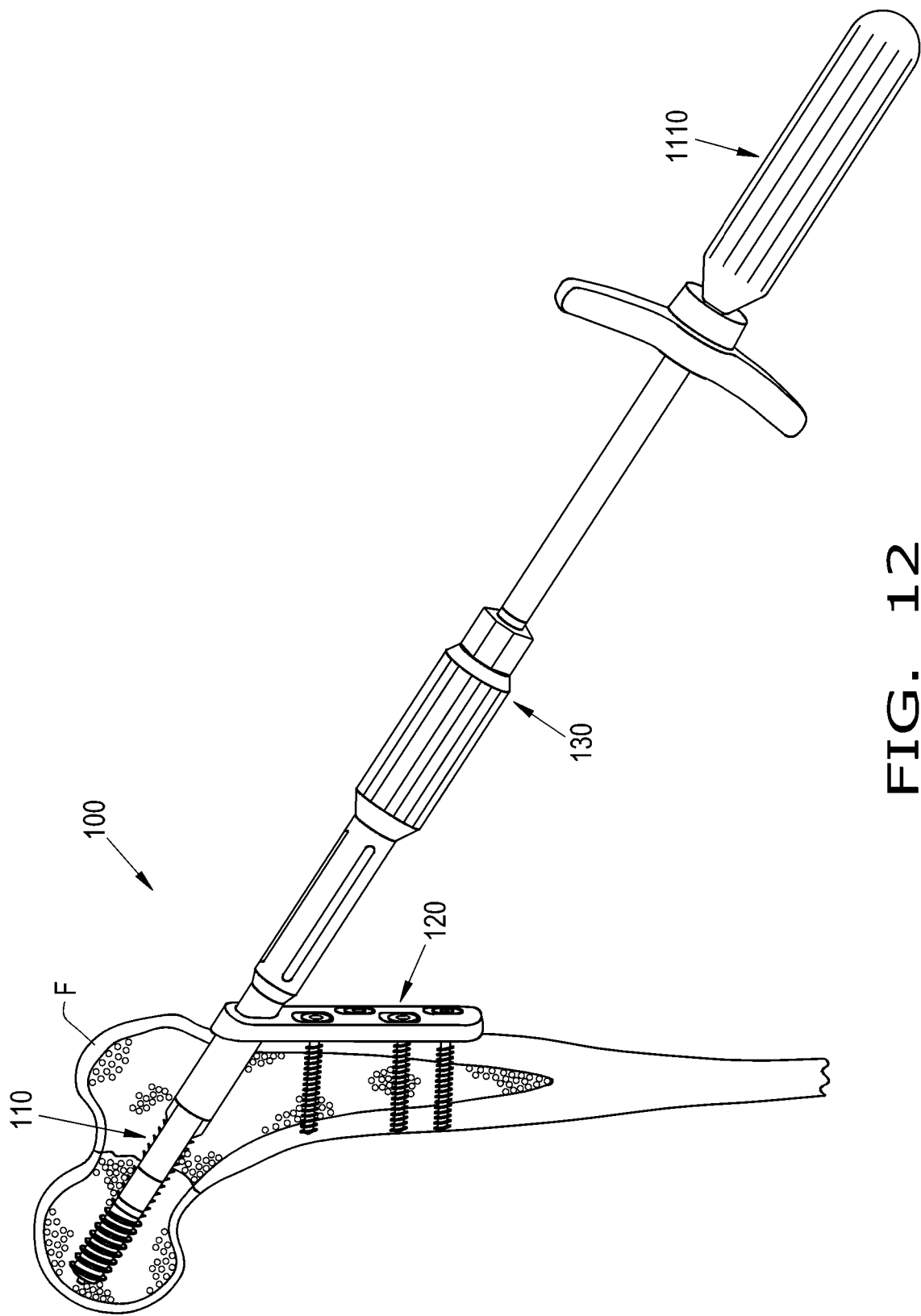
FIG. 12 is a perspective view of the orthopaedic trauma treatment system of FIGS. 1-6 and 10-11 with the injector placed in the cannulation of the lag screw.
Figures 13, 14:
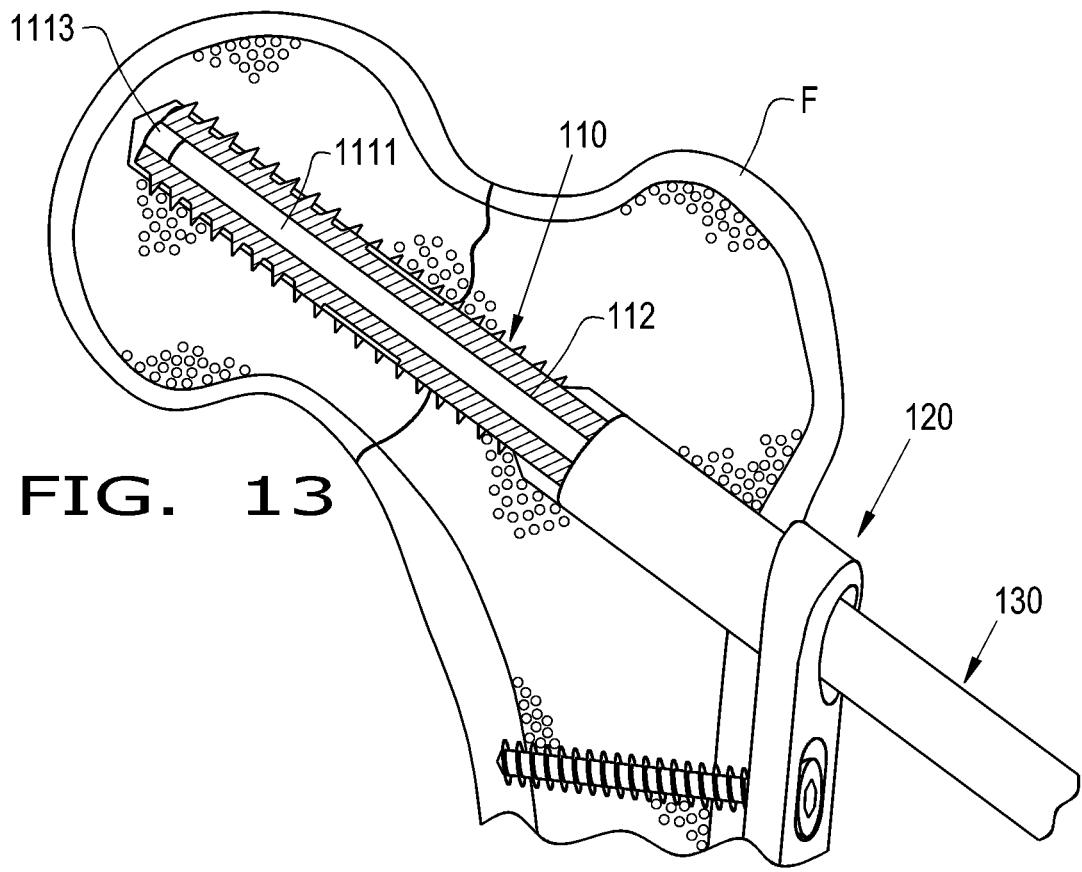
FIG. 13 is a partial cutaway view of the orthopaedic trauma treatment system of FIGS. 1-6 and 10-12 illustrating the injector placed in the cannulation of the lag screw.
FIG. 14 is a partial cutaway view of the orthopaedic trauma treatment system of FIGS. 1-6 and 10-13 illustrating openings of the injector placed in the cannulation of the lag screw to deliver therapeutic agent to the cannulation.

To deliver therapeutic agents, a guide rod 1010 that is used to help guide the lag screw 110 in the femur F is removed from the cannulation 112 within the device body 111 of the lag screw 110 and from the installation assembly 130, as illustrated in FIG. 10. A therapeutic agent injector 1110, first illustrated in FIG. 11, is then placed in a cannulation 135 of the installation assembly 130 and the cannulation 112 of the device body 111 of the lag screw 110. The injector 1110 may include an elongated cylindrical tube 1111 that is capped at one end 1112 by a cap 1113. The cap 1113 can help keep therapeutic agents within the injector 1110 during placement and also prevent bone material from entering the tube 1111 during placement, which can fill and block the tube 1111. Once the injector 1110 is placed within the lag screw 110, as illustrated in FIGS. 12-14, therapeutic agent introduced into the tube 1111 may travel through openings 1114 formed in the tube 1111 and through pores of the porous ingrowth material regions 117A, 117B, which are fluidly coupled to the cannulation 112, to reach the surrounding tissues, i.e., one or more regions outside the device body 111. Thus, the porous ingrowth material regions 117A, 117B can also be placed in areas of the lag screw 110 for targeted delivery of therapeutic agents to various regions of the implantation site.

Figure 15:
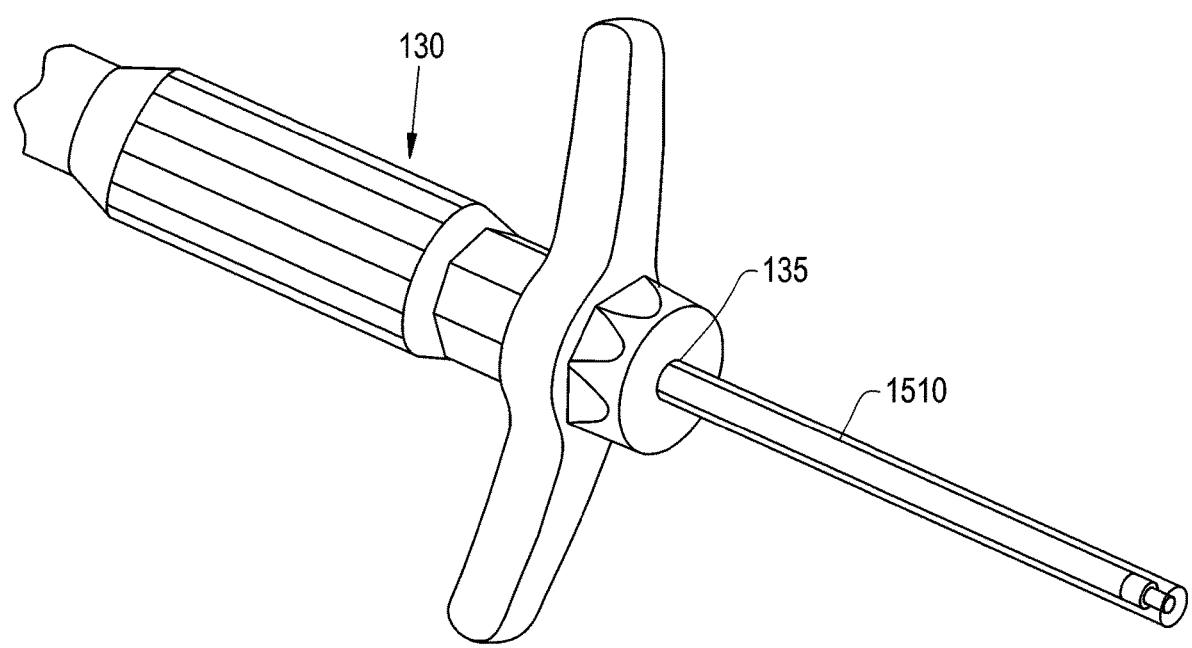
FIG. 15 is a perspective view of a reservoir being inserted into a cannulation of an installation assembly for insertion into the cannulation of the lag screw of FIGS. 1-6.
Figure 16:
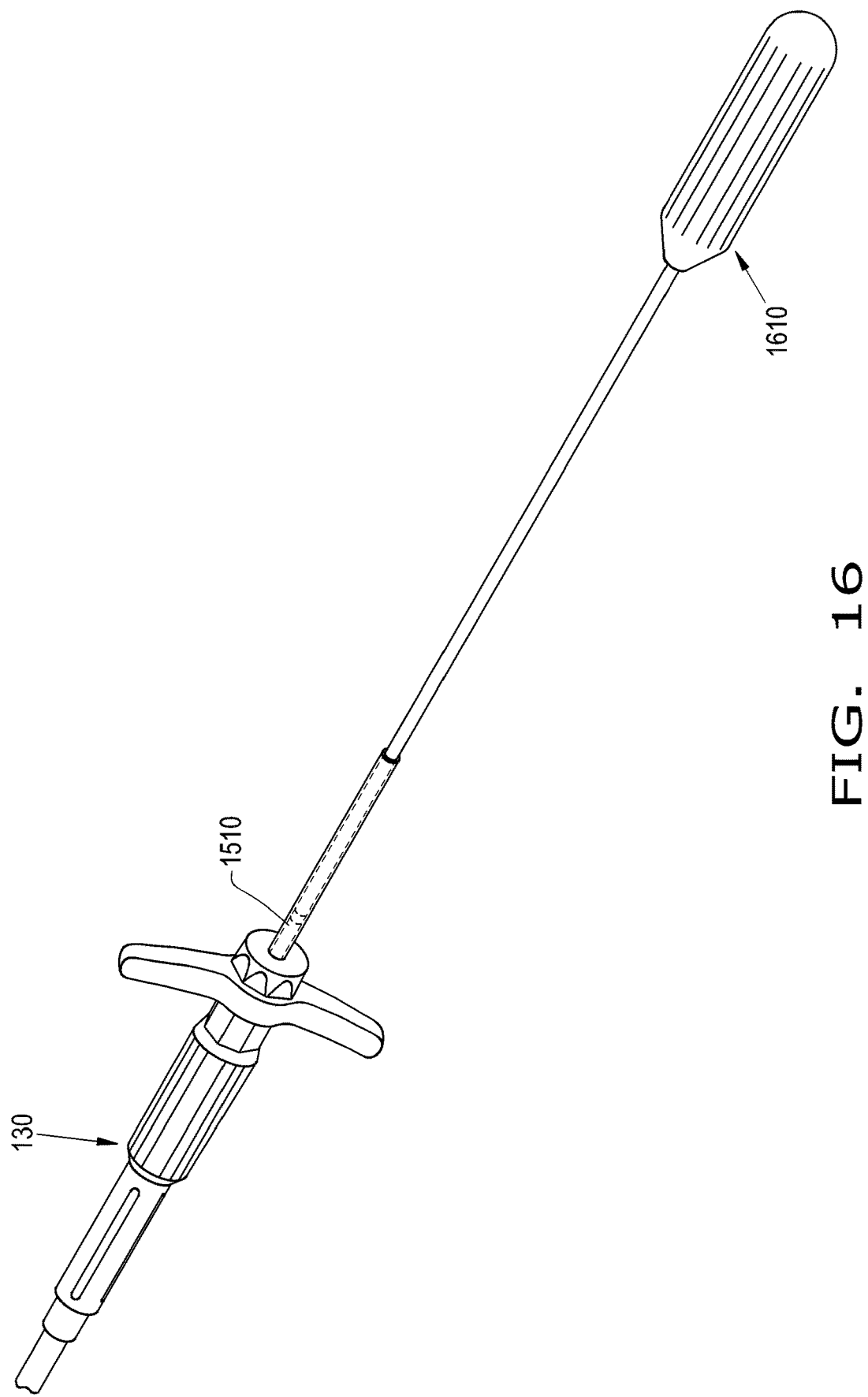
FIG. 16 is a perspective view of the reservoir and the installation assembly of FIG. 15 with a push rod being used to push the reservoir into the cannulation of the installation assembly.
Figure 17:
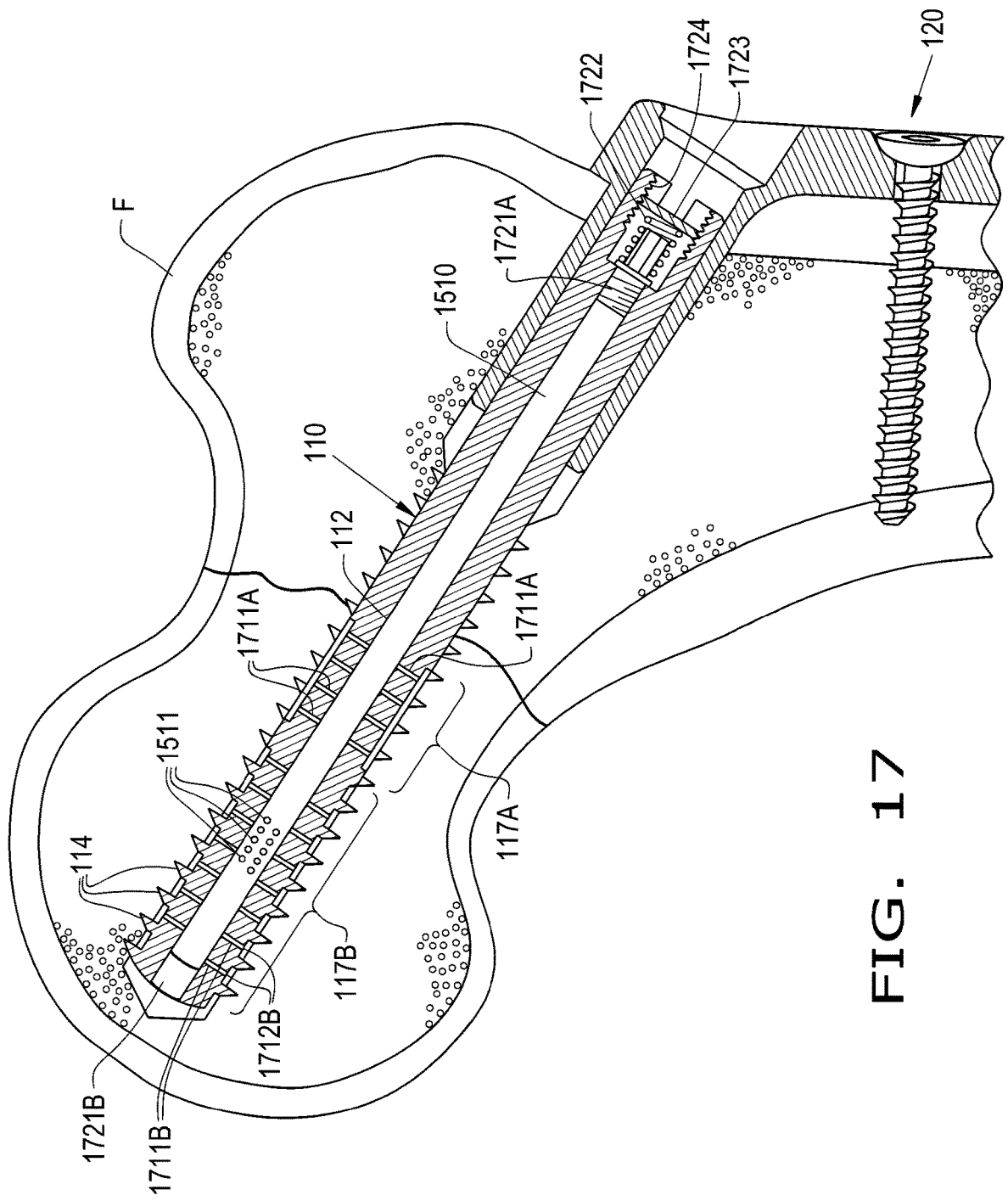
FIG. 17 is a cross-sectional view of the orthopaedic trauma treatment system of FIGS. 1-6 and the bone into which the trauma treatment system is implanted after the reservoir of FIGS. 15-16 is inserted into the cannulation of the lag screw.

In some embodiments, and referring now to FIGS. 15-17, a reservoir 1510 of therapeutic agent is placed in the cannulation 112 of the lag screw 110 for therapeutic agent delivery to the implantation site. The reservoir 1510 can be pushed into the cannulation 135 of the installation assembly 130 and then pushed into the cannulation 112 of the lag screw 110 by a push rod 1610 Illustrated in FIG. 16). Once placed in the cannulation 112 of the lag screw 110, as illustrated in FIG. 17, therapeutic agent in the reservoir 1510 can travel through openings 1511 in the reservoir 1510 and the porous ingrowth material regions 117A, 117B to reach surrounding tissue of the implantation site.

As illustrated in FIG. 17, the device body 111 may include one or more fluid channels 1711A, 1711B, illustrated as a plurality of fluid channels, formed in the exterior surface 115 of the device body 111 and fluidly coupled to the cannulation 112. Some of the fluid channels, such as fluid channels 1711A, may be fluidly coupled to the porous ingrowth material region 117A that is located on an unthreaded portion of the device body 111 to fluidly couple the porous ingrowth material region 117A to the cannulation 112 for therapeutic agent delivery. Some of the fluid channels, such as fluid channels 1711B, may be formed to define openings 1712B that are located between two adjacent threads 114 so the fluid channels 1711B fluidly couple the porous ingrowth material regions 117B to the cannulation 112 for therapeutic agent delivery. When the device body 111 comprises a substantially non-porous, or minimally porous, material, the fluid channels 1711A, 1711B may represent the primary travel path for therapeutic agent, or other fluids, between the porous ingrowth material regions 117A, 117B and the cannulation 112. It should be appreciated that, when the device body 111 comprises a porous material, one or more fluid channels may still be included as a secondary, or primary, travel path between the cannulation 112 and the porous ingrowth material regions 117A, 117B.

In some embodiments, one or more plugs, illustrated as two plugs 1721A, 1721B, are placed in the cannulation 112 and configured to create a fluid-tight seal with the cannulation 112 so fluid within the cannulation 112 does not travel past the plugs 1721A, 1721B. One of the plugs, such as plug 1721A, may be a plunger that is configured to displace within the cannulation 112 in order to apply pressure to fluid within the cannulation 112. For example, a spring 1722 may be included that bears on the plunger 1721A and is configured to maintain a fluid pressure on fluid held within the cannulation 112 by forcing the plunger 1721A toward the other plug 1721B within the cannulation 112. The spring 1722 may be held between the plunger 1721A and a cap 1723 that is placed over an entryway 1724 to the cannulation 112; in some embodiments, the spring 1722 is a part of the cap 1723 and bears on the plunger 1721A when the cap 1723 threads into the entryway 1724.

Figure 18:
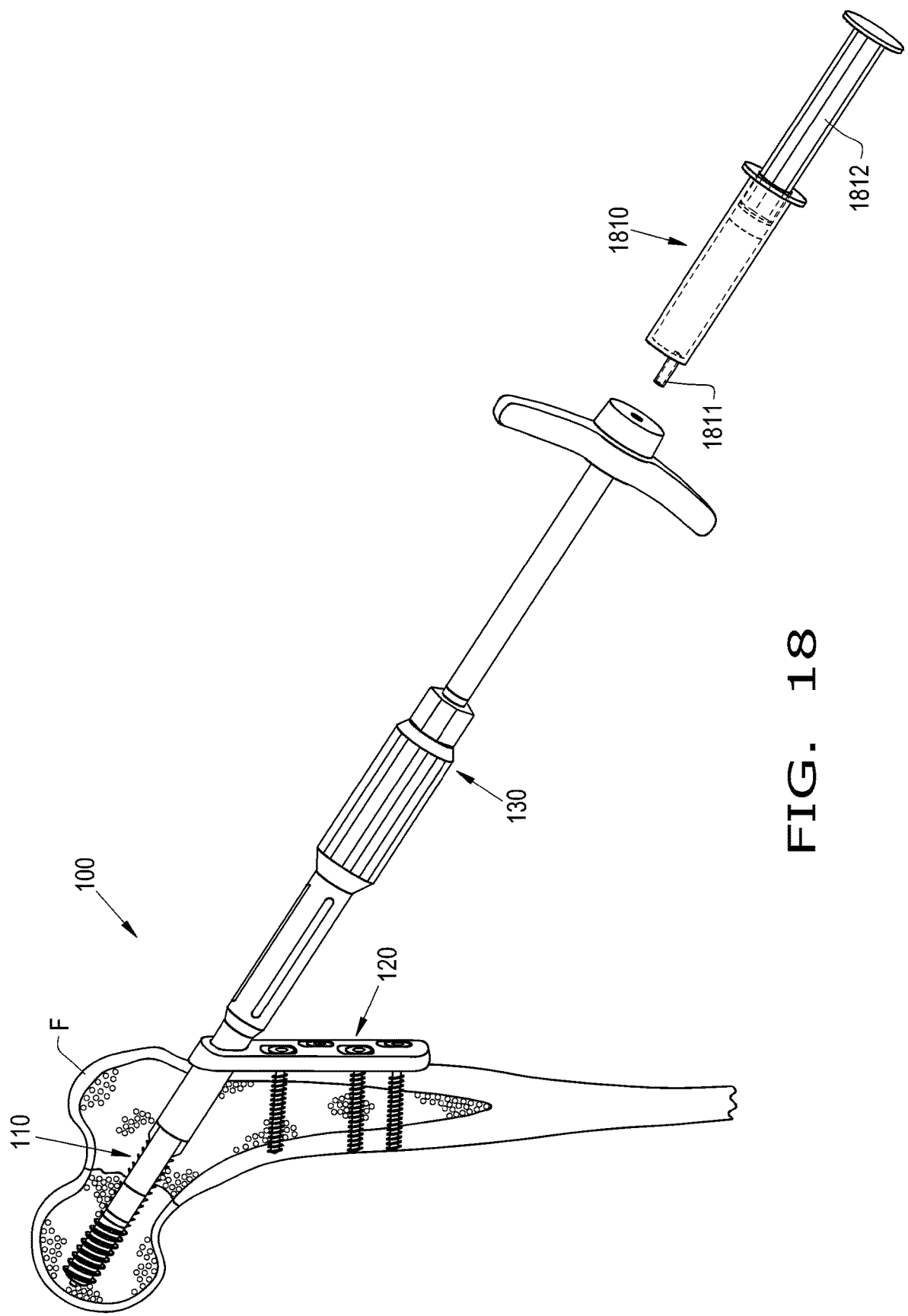
FIG. 18 is a perspective view of the orthopaedic trauma treatment system of FIGS. 1-6 being coupled to a syringe to deliver therapeutic agent.

In some embodiments, and referring now to FIG. 18, a syringe 1810 full of therapeutic agent can be coupled to the cannulation 135 of the installation assembly 130 and the cannulation 112 of the lag screw 110 to deliver therapeutic agent. Once a delivery port 1811 of the syringe 1810 is coupled to the cannulation 135 of the installation assembly 130, a plunger 1812 of the syringe 1810 can be depressed to force the therapeutic agent to the lag screw 110 for delivery through the porous ingrowth material regions 117A, 117B. The syringe 1810 may be held, for example, externally relative to the implantation site. While the syringe 1810 is shown as coupling to the installation assembly 130 for therapeutic agent delivery, it should be appreciated that the syringe 1810 can directly couple to the cannulation 112 of the lag screw 110 after implantation to deliver therapeutic agent.

Figure 19:
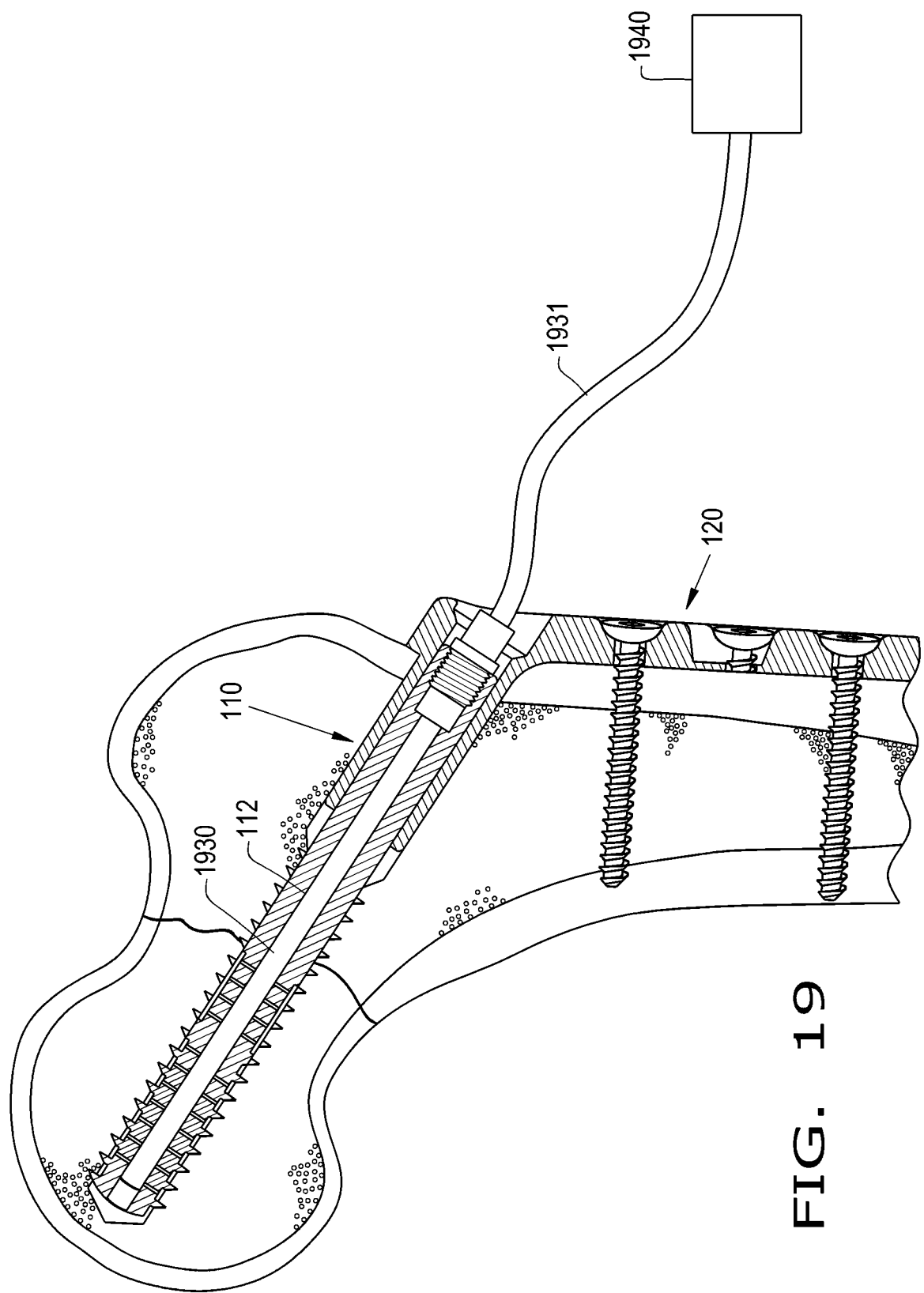
FIG. 19 is a cross-sectional view of the orthopaedic trauma treatment system of FIGS. 1-6 with a delivery reservoir placed inside the cannulation of the lag screw and coupled to an external reservoir for therapeutic agent delivery.

In some embodiments, and referring now to FIG. 19, a delivery reservoir 1930 can be placed inside the cannulation 112 of the lag screw 110. The delivery reservoir 1930 can include a tube 1931 that is configured to fluidly couple with the delivery reservoir 1930 at one end and with an external reservoir 1940 of therapeutic agent, such as the reservoir of an infusion pump or other type of pump, at the opposite end. In such an embodiment, the external reservoir 1940 can communicate therapeutic agent with the delivery reservoir 1930 via the tube 1931 to deliver the therapeutic agent to the tissue. Alternatively, the external reservoir 1940 can be used to refill the delivery reservoir 1930.

Figure 20:
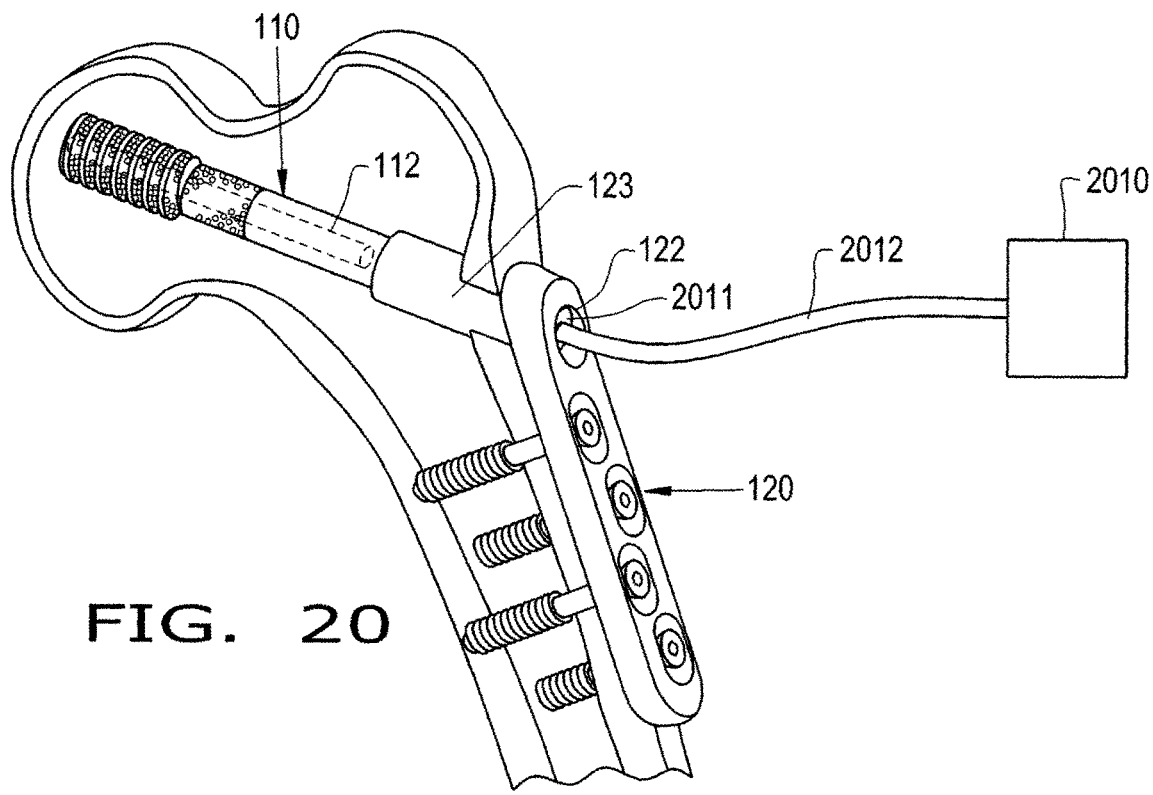
FIG. 20 is a perspective view of the orthopaedic trauma treatment system of FIGS. 1-6 implanted in a bone, which is illustrated in a partial cutaway view, with the cannulation of the lag screw directly fluidly coupled to an external reservoir to deliver therapeutic agent.

In some embodiments, and referring now to FIG. 20, an external reservoir 2010 can be coupled to the cannulation 112 of the lag screw 110 directly to deliver therapeutic agent. The external reservoir 2010 can include a plug 2011 that fits within an interface opening 122 formed in the bone plate 120 and is connected to a source of therapeutic agent by a tube 2012. Therapeutic agent can be pressurized through the tube 2012 into the lag screw 110 via a neck 123 of the bone plate 120 for delivery through the porous ingrowth material regions 117A, 117B.

Figure 21:
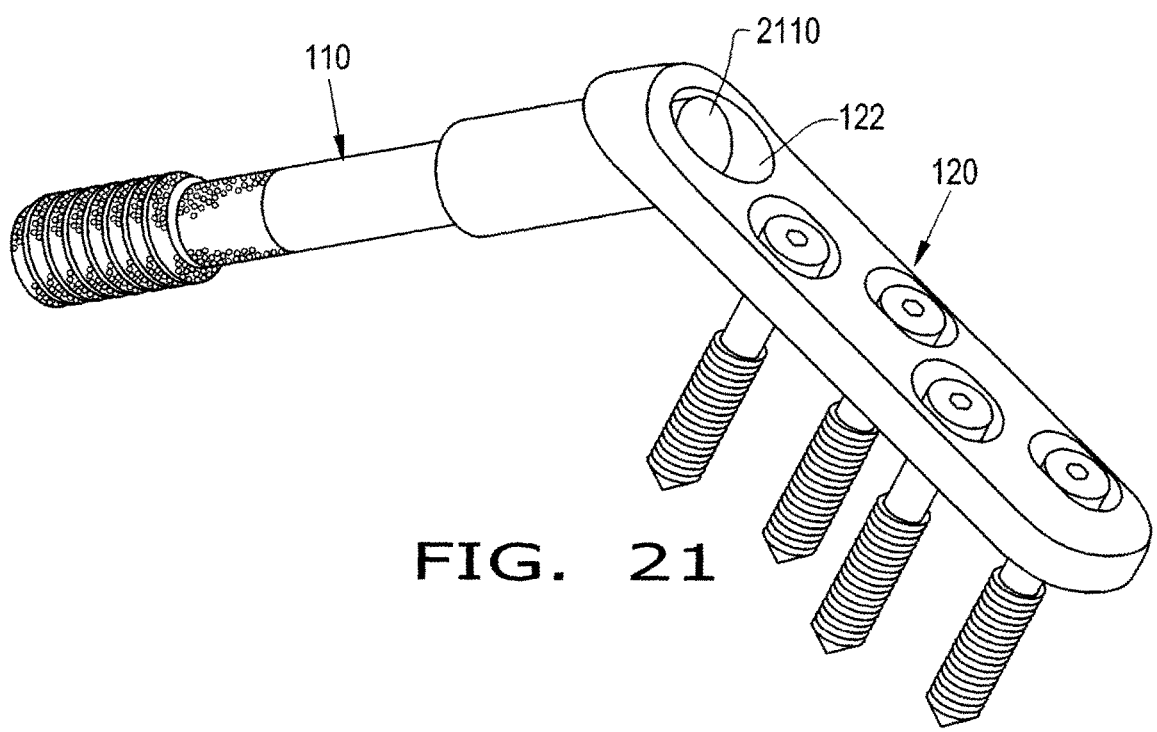
FIG. 21 is a perspective view of the orthopaedic trauma treatment system of FIGS. 1-6 after the cannulation of the lag screw has been filled with a therapeutic agent and an interface opening of the bone plate is plugged with a stopper.

In some embodiments, and referring now to FIG. 21, the lag screw 110 can be loaded with therapeutic agent after implantation. After the lag screw 110 is loaded with therapeutic agent, the interface opening 122 formed in the bone plate 120 can be plugged with a stopper 2110 so the therapeutic agent does not leak out through the interface opening 122.

From the foregoing, it should be appreciated that the orthopaedic trauma treatment systems 100, 700, 800, 900 formed in accordance with the present disclosure can be modified in many different ways to deliver therapeutic agents to the tissue at and surrounding the implantation site. The delivery of therapeutic agents can increase the healing rate of the bone and further reduce the risk of implant failure.

Figure 22:
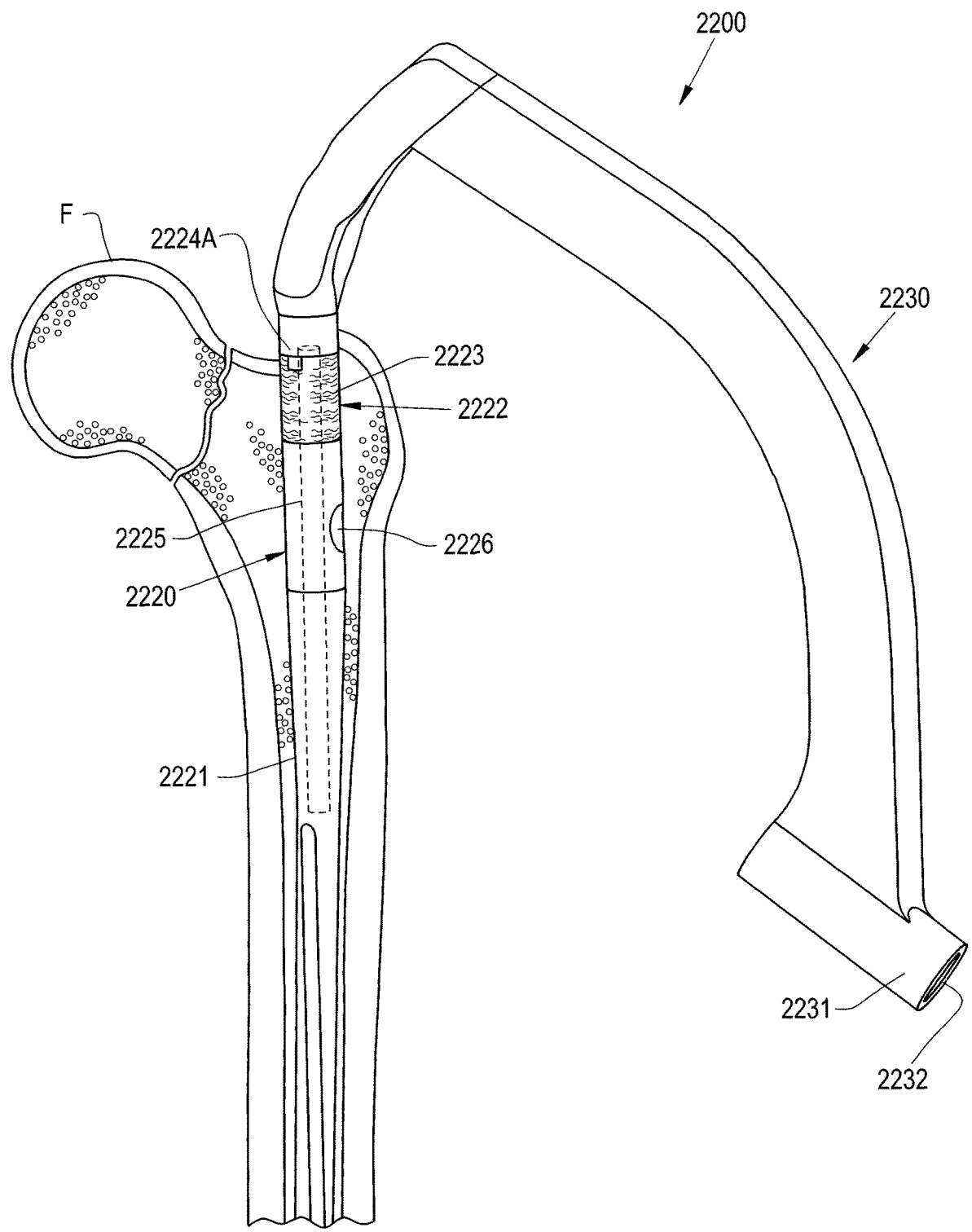
FIG. 22 is a perspective view of another exemplary embodiment of an orthopaedic trauma treatment system provided according to the present invention that includes an intramedullary nail implanted in a bone, which is illustrated in a partial cutaway view, and a jig attached to the intramedullary nail.
Figure 23:
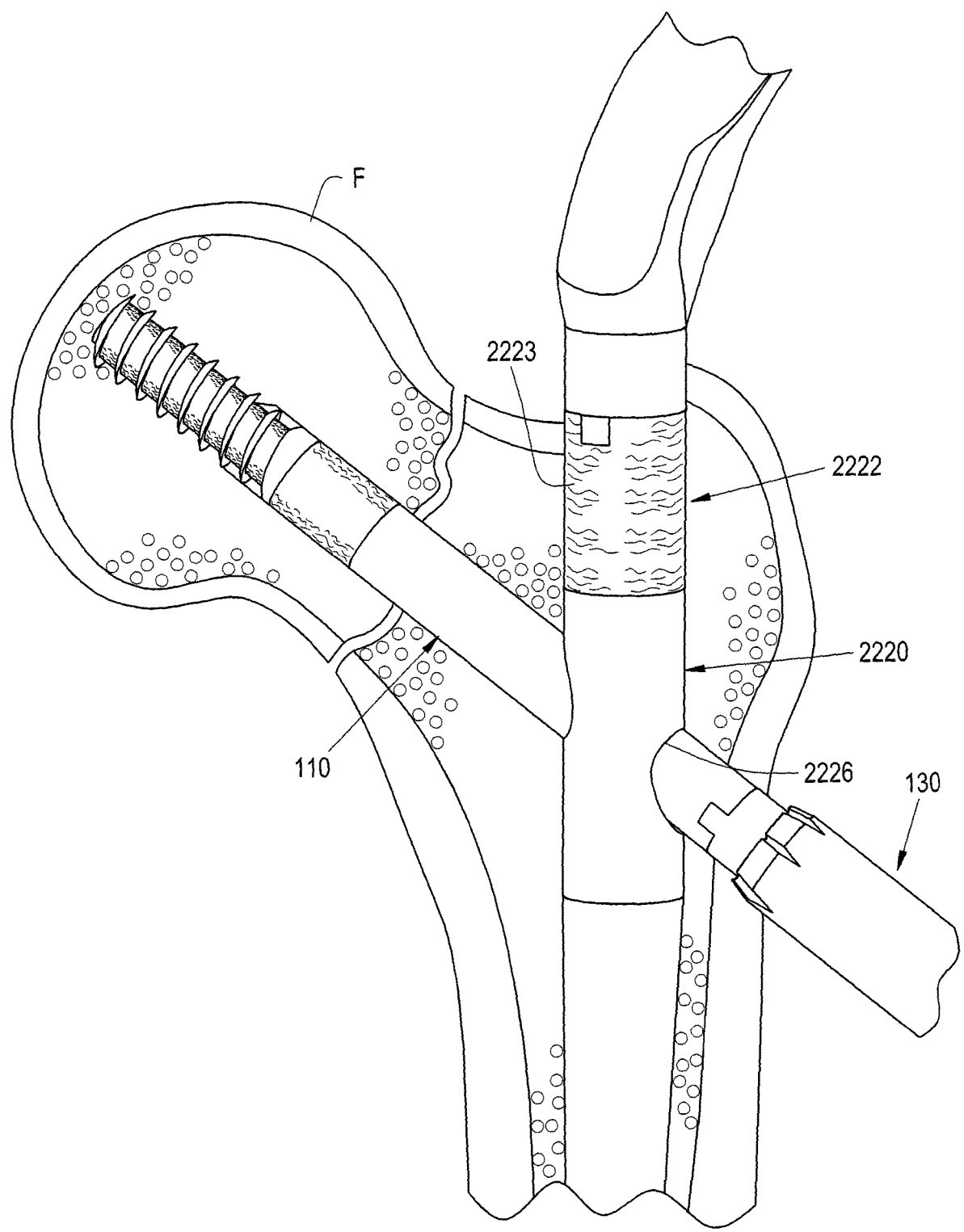
FIG. 23 is a perspective view of the orthopaedic trauma treatment system of FIG. 22 with the lag screw of FIGS. 1-6 coupled to the intramedullary nail and implanted in the bone.

Referring now to FIGS. 22-23, another exemplary embodiment of an orthopaedic trauma treatment system 2200 is illustrated that includes a second device in the form of an intramedullary (IM) nail 2220 that is coupled with the lag screw 110 of FIGS. 1-6. It should be appreciated that the IM nail 2220 of the orthopaedic trauma treatment system 2200 of FIGS. 22-23 may be used instead of the bone plate 120 of the system 100 of FIGS. 1-6. As can be seen, the IM nail 2220 can be implanted in the femoral shaft and include a device body 2221 that comprises a substantially non-porous or minimally porous material, such as non-porous titanium, and an ingrowth portion 2222 that comprises a porous ingrowth material region 2223, such as the previously described OSTEOSYNC®. The ingrowth portion 2222 may be placed adjacent to a longitudinal end 2224A of the IM nail 2220 such that the ingrowth portion 2222 substantially resides in and adjacent to the greater trochanter of the femur F. The IM nail 2220 may include a cannulation 2225 that extends from the longitudinal end 2224A of the device body 2221 to an opposite longitudinal end 2224B of the device body 2221 and is fluidly coupled to the porous ingrowth material region 2223 for therapeutic agent delivery. In some embodiments, the porous ingrowth material region 2223 defines a length that is between 1.0 and 2.0 inches, such as 1.5 inches, which has been found to provide good fixation characteristics. A lag screw opening 2226 is formed in the device body 2221 of the IM nail 2220 to accept and hold the lag screw 110 when implanted, as illustrated in FIG. 23. In some embodiments, a jig 2230 is coupled to the IM nail 2220 to assist a surgeon with implantation of the lag screw 110 using the installation assembly 130. The jig 2230 may include a targeting portion 2231 that includes a targeting opening 2232 aligned with the lag screw opening 2226. Many such jigs are known, so further description is omitted for brevity.

As previously described, it has been found that the main failure mode for orthopaedic trauma treatment systems occurs near the femoral head. It has also been found that, when IM nails are used, the main failure mode occurs near the greater trochanter. By placing the porous ingrowth material region 2223 on the IM nail 2220 such that the porous ingrowth material region 2223 will reside near the greater trochanter when implanted, additional fixation of the IM nail 2220 can occur in this region to stably fixate the orthopaedic trauma treatment system 2200 and reduce the risk of failure.

Figure 24:
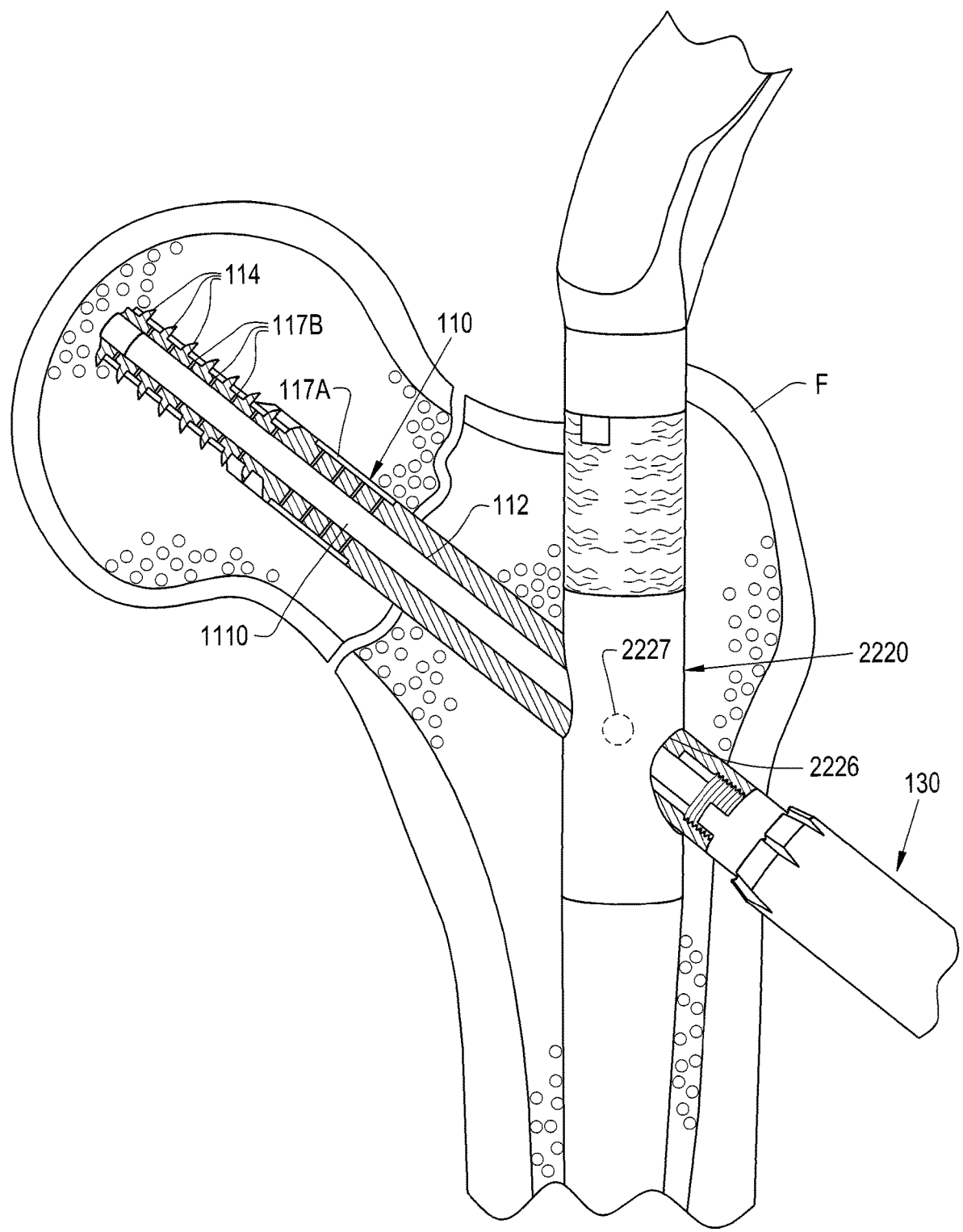
FIG. 24 is a partial cutaway view of the orthopaedic trauma treatment system of FIGS. 22-23 with the injector of FIGS. 11-14 placed in the cannulation of the lag screw for therapeutic agent delivery.

Referring now to FIG. 24, the orthopaedic trauma treatment system 2200 of FIGS. 22-23 is shown with the injector 1110 illustrated in FIGS. 11-14 placed in the cannulation 112 of the lag screw 110 to deliver therapeutic agent to tissue surrounding the lag screw 110 through the porous ingrowth material regions 117A, 117B, as previously described. In some embodiments, the ingrowth portion 2222 of the IM nail 2220 is also fluidly coupled to the injector 1110 via a port 2227 formed in the IM nail 2220 to deliver therapeutic agent to the cannulation 2225 of the IM nail 2220 and thus tissue surrounding the ingrowth portion 2222 of the IM nail 2220.

Figure 25:
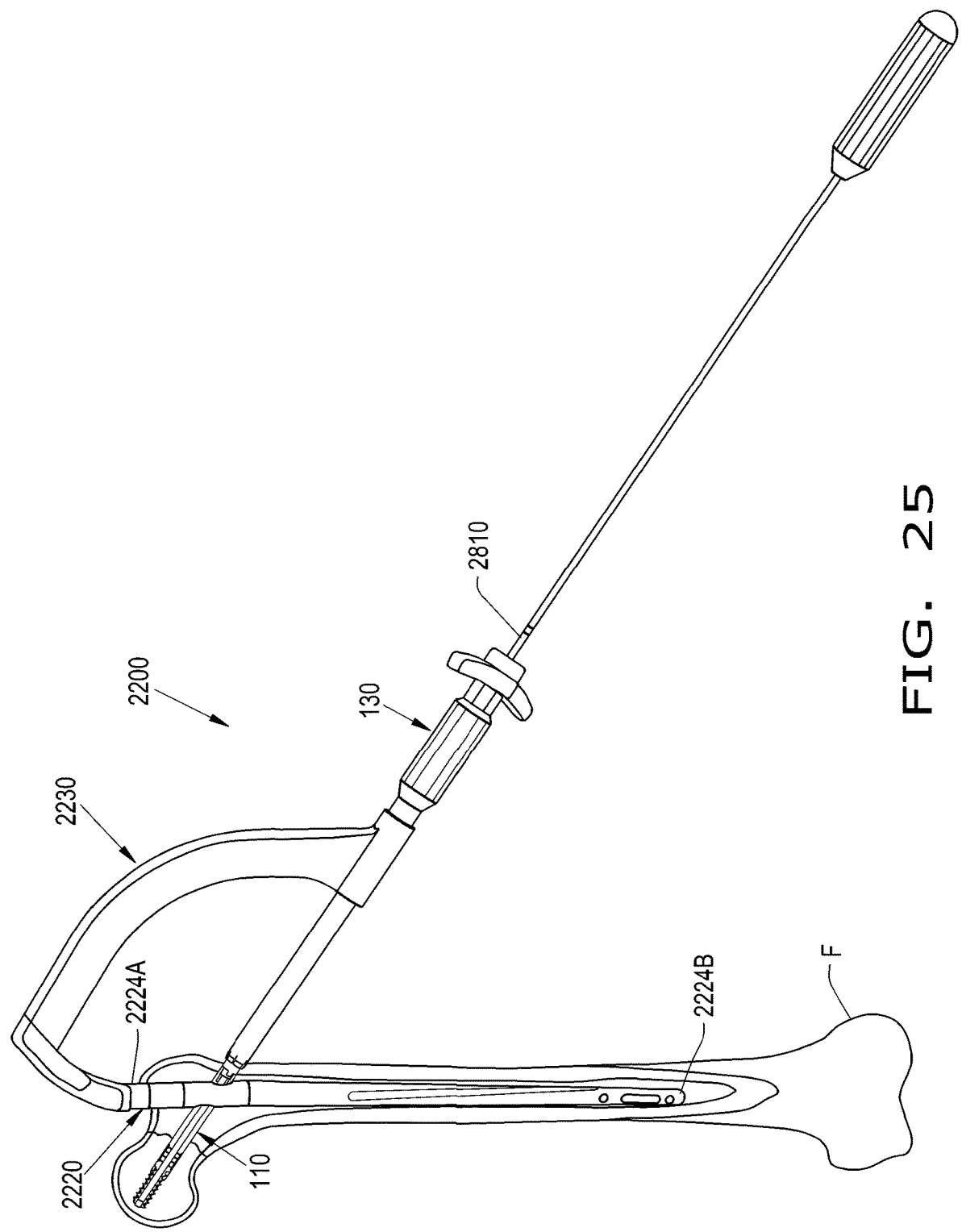
FIG. 25 is a perspective view of orthopaedic trauma treatment system of FIGS. 22-23 with a reservoir being inserted into the cannulation of the lag screw.
Figure 26:
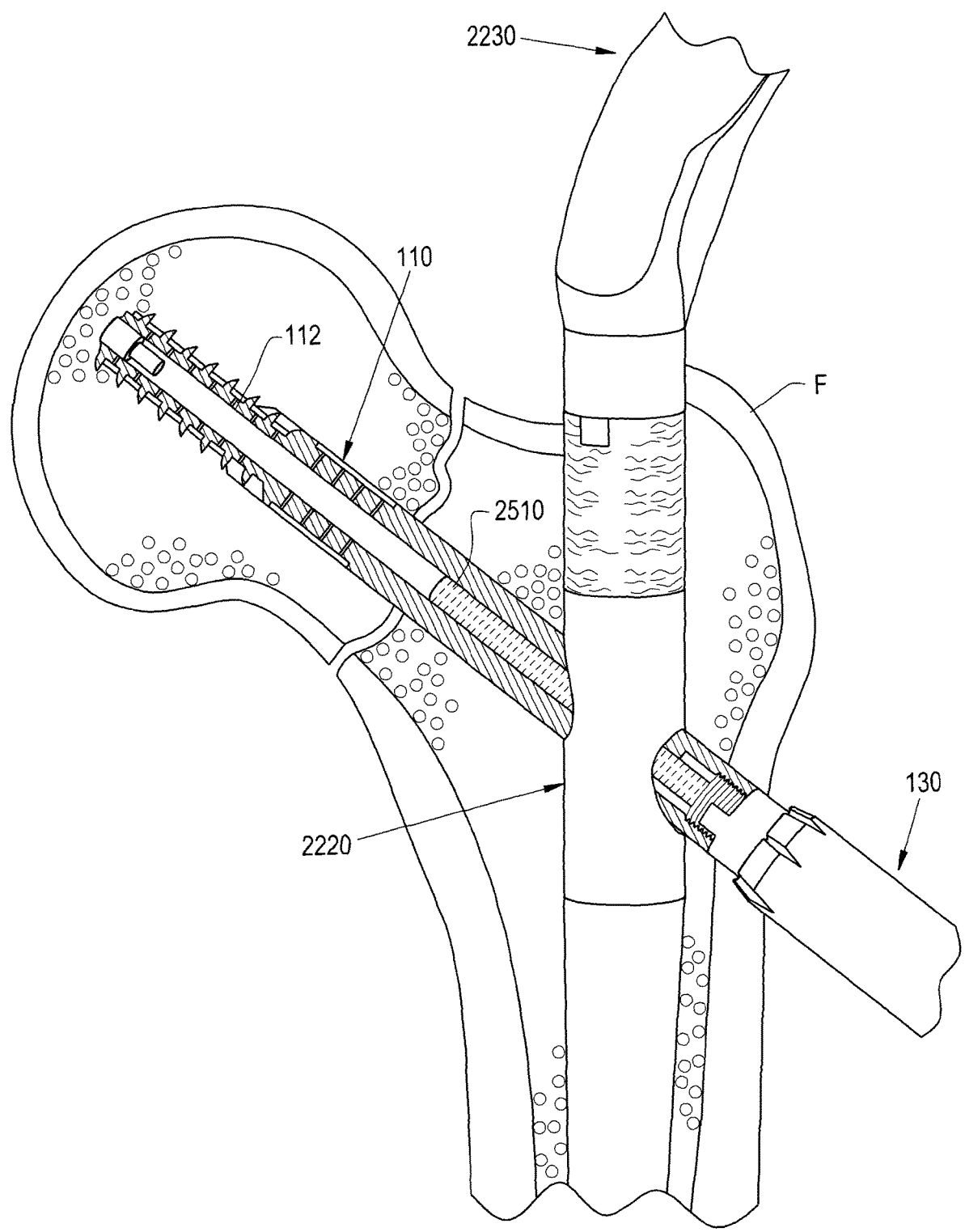
FIG. 26 is a cross-sectional view of the orthopaedic trauma treatment system of FIG. 25 with the reservoir being inserted into the cannulation of the lag screw.
Figure 27:
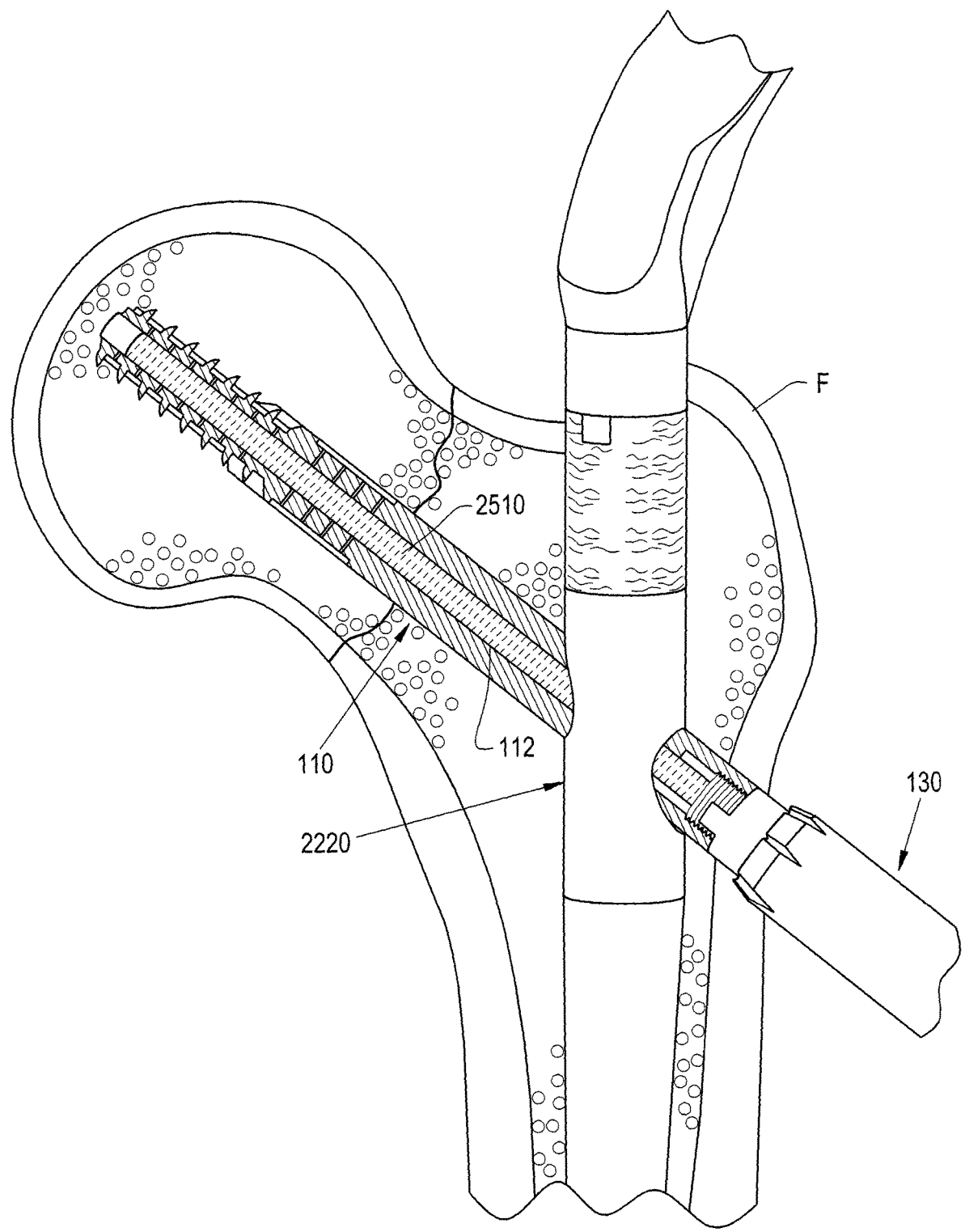
FIG. 27 is a cross-sectional view of the orthopaedic trauma treatment system of FIGS. 25-26 with the reservoir fully inserted in the cannulation of the lag screw.

Referring now to FIGS. 25-27, the orthopaedic trauma treatment system 2200 of FIGS. 22-23 is shown with a reservoir 2510 placed in the cannulation 112 of the lag screw 110, similarly to FIGS. 15-17.

Figure 28:
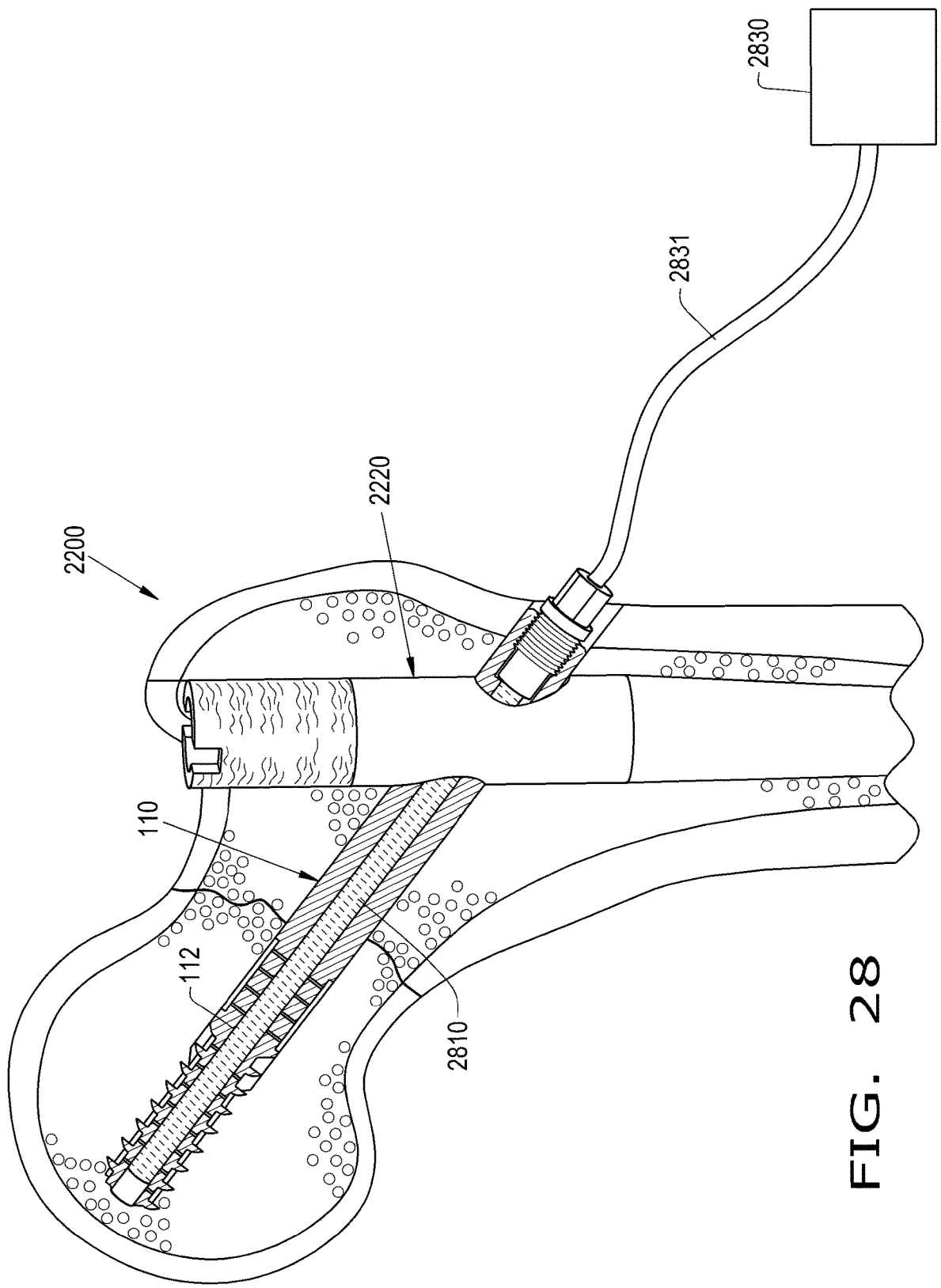
FIG. 28 is a cross-sectional view of the orthopaedic trauma treatment system of FIGS. 22-23 with a delivery reservoir placed in the cannulation of the lag screw and fluidly coupled to an external reservoir.

Referring now to FIG. 28, the orthopaedic trauma treatment system 2200 of FIGS. 22-23 is shown with a delivery reservoir 2810 placed in the cannulation 112 of the lag screw 110 that is coupled to an external reservoir 2830 by a tube 2831, similarly to FIG. 19.

Figure 29:
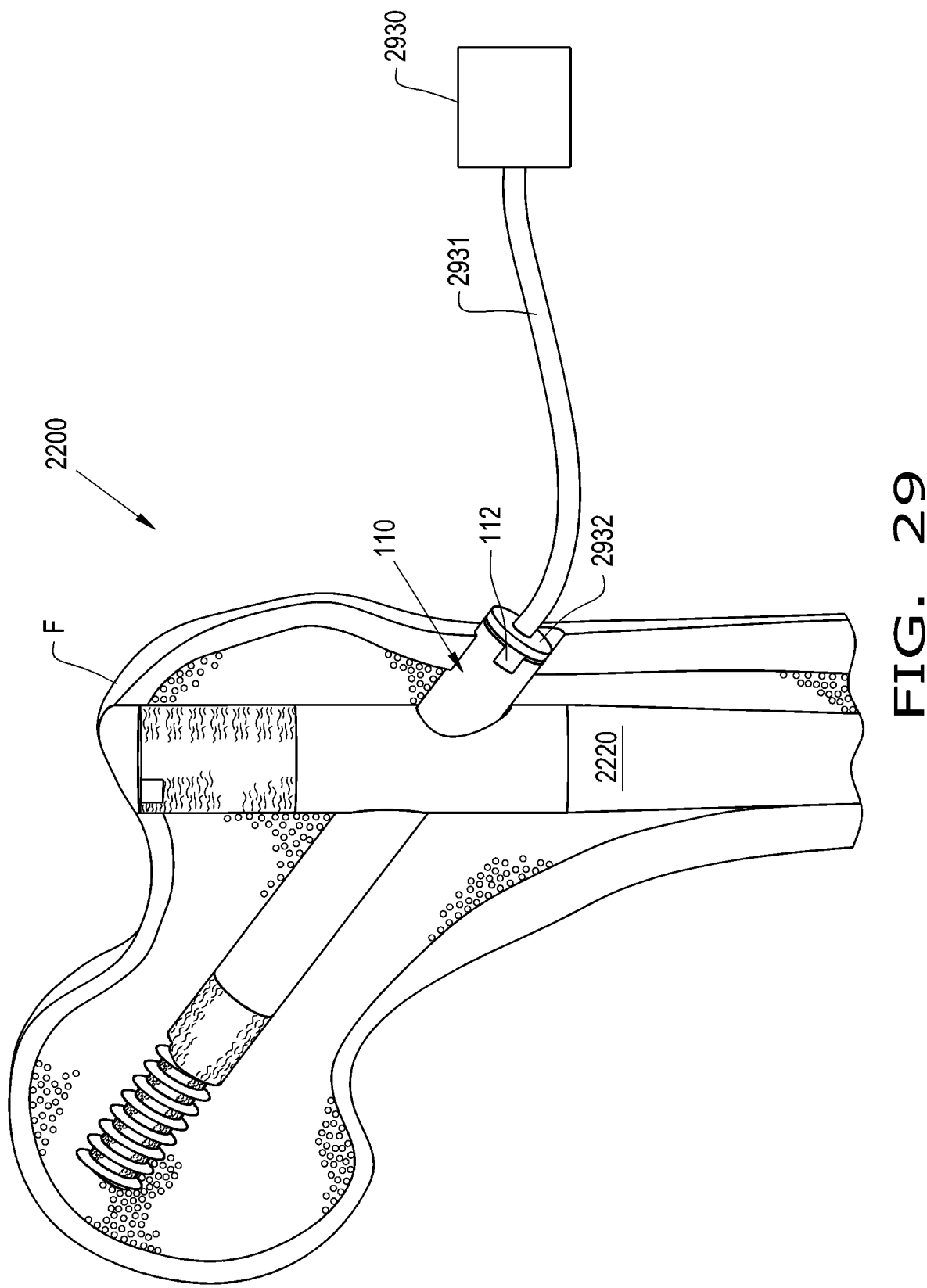
FIG. 29 is a cross-sectional view of the orthopaedic trauma treatment system of FIGS. 22-23 with an external reservoir directly fluidly coupled to the cannulation of the lag screw.

Referring now to FIG. 29, the orthopaedic trauma treatment system 2200 of FIGS. 22-23 is shown with an external reservoir 2930 directly coupled to the cannulation 112 of the lag screw 110 via a tube 2931 and a plug 2932.

From the foregoing, it should be appreciated that the orthopaedic trauma treatment system 2200 provided according to the present invention may be configured in many different ways to deliver therapeutic agent to tissue surrounding the lag screw 110 and/or the IM nail 2220.

Figure 30:
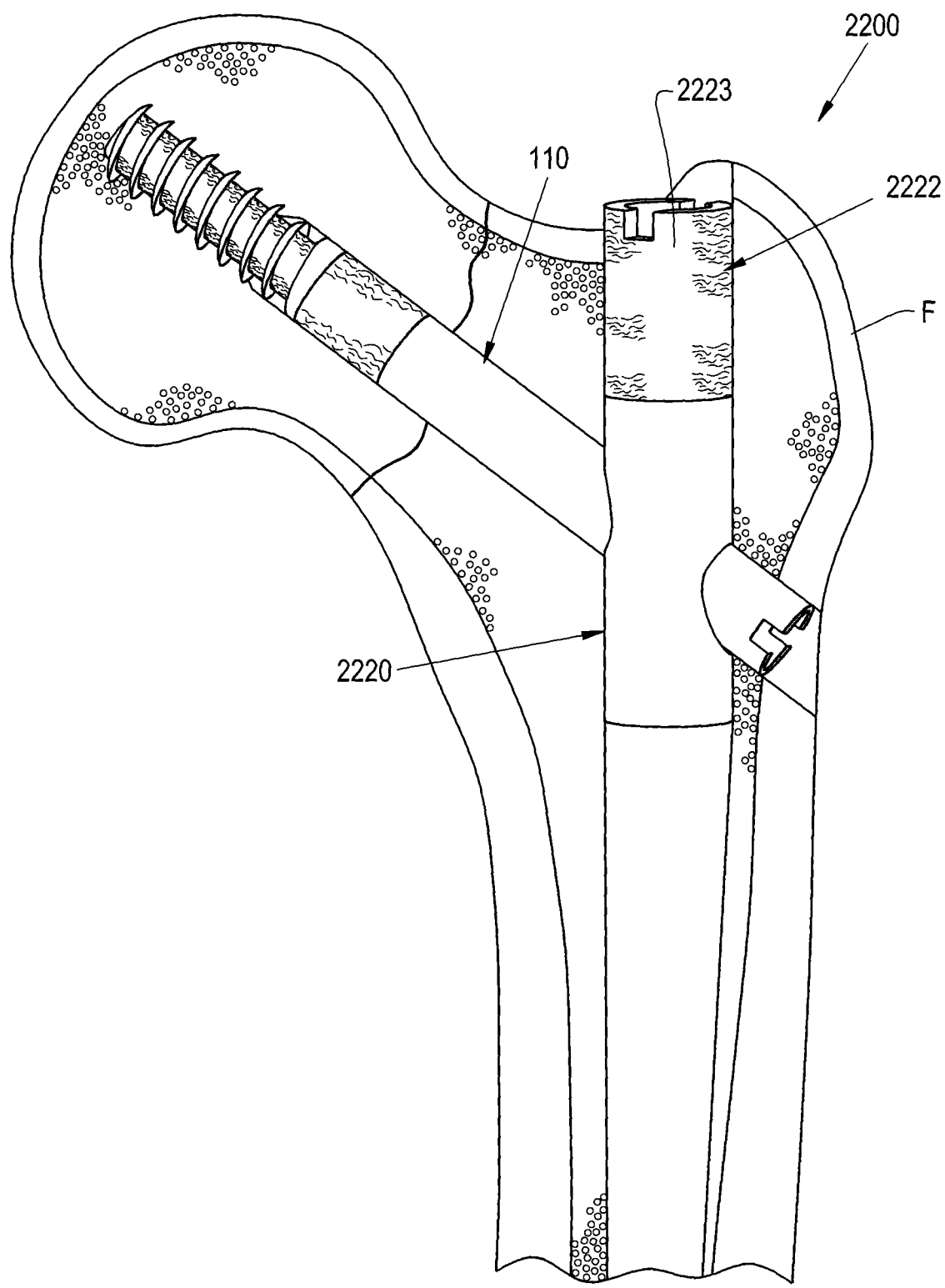
FIG. 30 is a partial cutaway view of the orthopaedic trauma treatment system of FIGS. 22-23 implanted in the bone without the jig attached.

Referring now to FIG. 30, the orthopaedic trauma treatment system 2200 of FIGS. 22-23 is illustrated without the jig 2230 attached. As can be seen, a nail bore is formed in the greater trochanter of the femur F in order to insert the IM nail 2220 and a screw bore is formed in the femoral shaft to insert the lag screw 110. Once implanted, the ingrowth portion 2222 of the IM nail 2220 may slightly protrude out of the greater trochanter due to the shape of the IM nail 2220 and the greater trochanter. Since the ingrowth portion 2222 is porous, a surgeon may readily cut through the protruding part of the ingrowth portion 2222 so the IM nail 2220 does not protrude out of the femur F. The lag screw 110 may also be implanted so an entirety of the lag screw 110 resides within the femur F.

Figure 31:
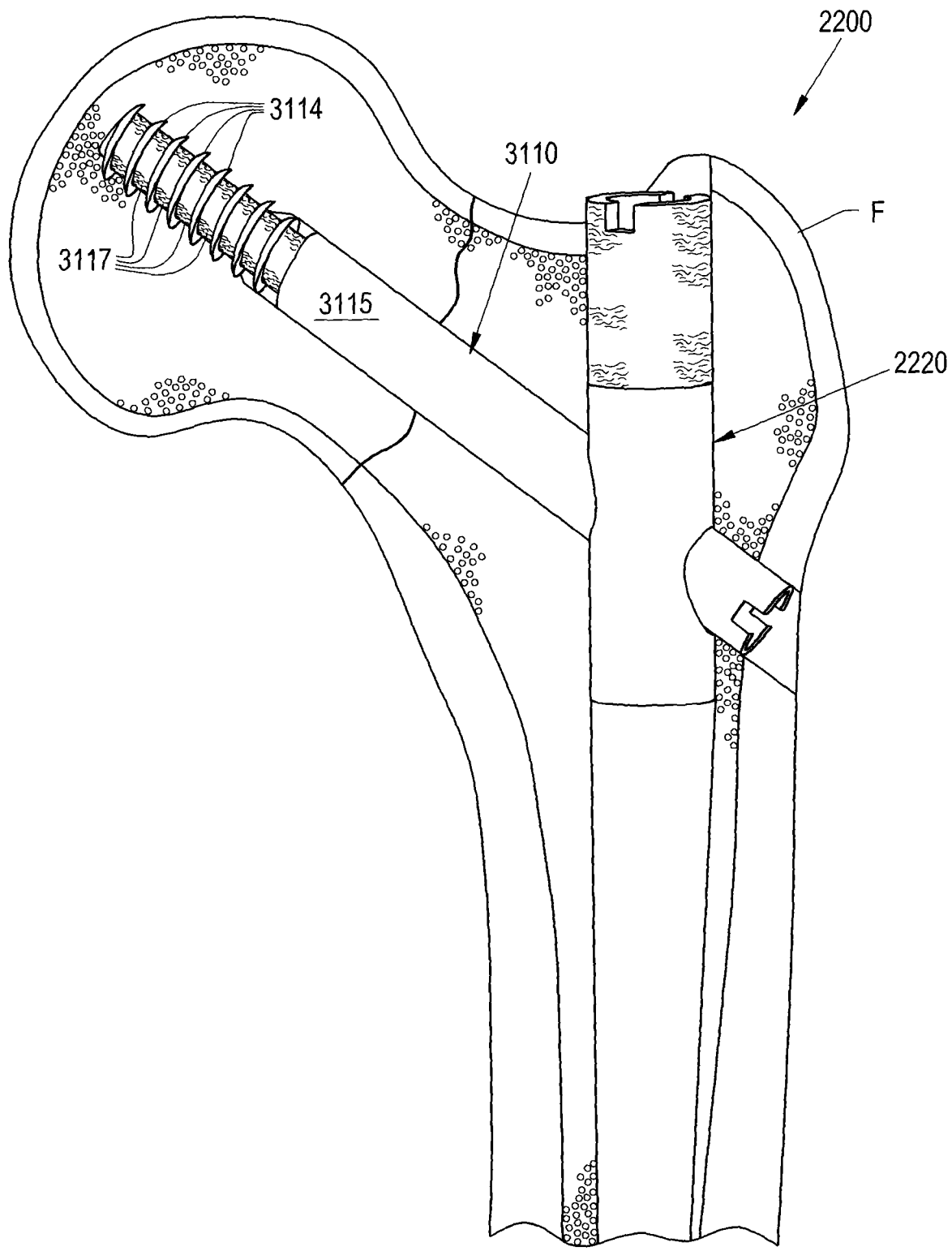
FIG. 31 is a partial cutaway view of the orthopaedic trauma treatment system of FIGS. 22-23 with an alternative embodiment of a lag screw that has porous ingrowth material regions placed between threads of the lag screw.

Referring now to FIG. 31, the orthopaedic trauma treatment system 2200 of FIGS. 22-23 is illustrated with an alternative embodiment of a lag screw 3110 that only has porous ingrowth material regions 3117 between threads 3114 formed in an exterior surface 3115 of the lag screw 3110. In all other respects, the lag screw 3110 may be similar to previously described lag screws, so further description is omitted for brevity.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for treating orthopaedic trauma, comprising:
a device body having an exterior surface and a cannulation formed therein that extends from one longitudinal end of the device body to an opposite longitudinal end of the device body;
at least one porous ingrowth material region associated with the exterior surface of the device body and fluidly coupled to the cannulation, the at least one porous ingrowth material region being configured to deliver a therapeutic agent from the cannulation to a region outside the device body; and
a reservoir configured to be removably inserted in the cannulation and to hold the therapeutic agent therein.

2. The device of claim 1, wherein the device body comprises at least one fluid channel that is formed in the exterior surface and is fluidly coupled to the cannulation.

3. The device of claim 2, wherein the device body comprises a plurality of threads formed in the exterior surface.

4. The device of claim 3, wherein the at least one fluid channel defines an opening located between two adjacent threads of the plurality of threads.

5. The device of claim 3, wherein the at least one porous ingrowth material region is located between two adjacent threads of the plurality of threads.

6. The device of claim 5, wherein the at least one porous ingrowth material region comprises a plurality of porous ingrowth material regions, at least one of the porous ingrowth material regions being disposed on an unthreaded portion of the device body.

7. The device of claim 2, wherein the at least one fluid channel fluidly couples the at least one porous ingrowth material region to the cannulation.

8. The device of claim 7, wherein the device body comprises a substantially non-porous material.

9. The device of claim 2, further comprising at least one plug placed in the cannulation and configured to create a fluid-tight seal with the cannulation.

10. The device of claim 9, wherein the at least one plug comprises a plunger configured to displace within the cannulation.

11. The device of claim 10, further comprising a spring bearing on the plunger and configured to maintain a fluid pressure on fluid held within the cannulation.

12. The device of claim 9, wherein the at least one plug is configured to couple with an external fluid reservoir to receive fluid within the cannulation.

13. The device of claim 1, wherein the reservoir comprises a plurality of openings configured to allow travel of the therapeutic agent out of the reservoir.

14. The device of claim 1, wherein the at least one porous ingrowth material region is located on the exterior surface of the device body such that the at least one porous ingrowth material region resides near a bone fracture in a bone following implantation in the bone.

15. The device of claim 1, wherein the at least one porous ingrowth material region is located adjacent to one of the longitudinal ends of the device body.

16. The device of claim 15, wherein the at least one porous ingrowth material region defines a length that is between 1.0 and 2.0 inches.

17. An orthopaedic trauma treatment system, comprising:
a first device comprising:
a first device body having an exterior surface and a cannulation formed therein that extends from one longitudinal end of the device body to an opposite longitudinal end of the device body;
at least one first porous ingrowth material region associated with the exterior surface of the first device body and fluidly coupled to the cannulation, the at least one first porous ingrowth material region being configured to deliver a therapeutic agent from the cannulation to a region outside the first device body; and
a reservoir configured to be removably inserted in the cannulation and to hold the therapeutic agent therein; and
a second device coupled to the first device and comprising a second device body having at least one second porous ingrowth material region.

18. The trauma treatment system of claim 17, wherein the second device body has a cannulation formed therein that is fluidly coupled with the at least one second porous ingrowth material region.

19. The trauma treatment system of claim 17, wherein the first device is a screw comprising a plurality of threads and the second device is a nail.

\* \* \* \* \*